(12) United States Patent
Samoylova et al.

(10) Patent No.: US 7,094,868 B2
(45) Date of Patent: Aug. 22, 2006

(54) PEPTIDES FOR RECOGNITION AND TARGETING OF GLIAL CELL TUMORS

(75) Inventors: Tatiana I. Samoylova, Auburn, AL (US); Valery A. Petrenko, Auburn, AL (US); Nancy R. Cox, Auburn, AL (US); Nancy E. Morrison, Auburn, AL (US); Henry J. Baker, Auburn, AL (US); Ludmila P. Globa, Auburn, AL (US)

(73) Assignee: Auburn University, Auburn, AL (US)

( * ) Notice: Subject to any disclaimer, the term of this patent is extended or adjusted under 35 U.S.C. 154(b) by 177 days.

(21) Appl. No.: 10/357,929

(22) Filed: Feb. 4, 2003

(65) Prior Publication Data

US 2003/0216322 A1 Nov. 20, 2003

Related U.S. Application Data

(60) Provisional application No. 60/354,118, filed on Feb. 4, 2002.

(51) Int. Cl.
  *C07K 7/04* (2006.01)
  *C07K 7/06* (2006.01)
  *C07K 5/00* (2006.01)
  *C07K 17/00* (2006.01)
  *C12Q 1/70* (2006.01)
  *G01N 33/574* (2006.01)
  *C12N 7/01* (2006.01)
  *C12N 15/00* (2006.01)

(52) U.S. Cl. ............... 530/328; 530/300; 530/329; 530/330; 530/333; 435/5; 435/7.23; 435/235.1; 435/320.1

(58) Field of Classification Search ............... 530/300, 530/328, 329, 330; 435/235.1, 320.1, 325.1
See application file for complete search history.

(56) References Cited

U.S. PATENT DOCUMENTS 6,395,873 B1   5/2002  Pierschbacher et al.
6,551,795 B1*  4/2003  Rubenfield et al.

FOREIGN PATENT DOCUMENTS

WO   WO 9957149 A2 * 11/1999
WO   WO 200122922 A2 *  4/2001
WO   WO 200124810 A1 *  4/2001

OTHER PUBLICATIONS

Zhang et al. Cancer Letters, 171(2):153-164, Oct. 10, 2001.*
Koivunen et al. Biotechnology, 13(3):265-270, Mar. 1995.*
Samoylova et al. Molecular Cancer Therapeutics, 2:1129-1137, 2003.*
Samoylova T. I., et al. "Targeting Peptides for Microglia Identified via Phage Display," Journal of Neuroimmunology, 2002, pp. 13-21, vol. 127(1-2).*
Akiyama, S., "Integrins in Cell Adhesion and Signaling," *Human Cell*, 1996, pp. 181-186, vol. 9(3).
Bafetti et al., "Intact Vitronectin Induces Matrix Metalloproteinase-2 and Tissue Inhibitor of Metalloproteinases-2 Expression and Enhanced Cellular Invasion by Melanoma Cells," *The Journal of Biological Chemistry*, 1998, pp. 143-149, vol. 273(1).
Barry, et al., "Toward Cell-Targeting Gene Therapy Vectors: Selection of Cell-Binding Peptides from Random Peptide-Presenting Phage Libraries," *Nature Medicine*, 1996, pp. 299-305, vol. 2(3).
Ruoslahti, E., "Integrins as Signaling Molecules and Targets for Tumor Therapy," *Kidney International*, 1997, pp. 1413-1417, vol. 51.
Zamir, et al., "Molecular Complexity and Dynamics of Cell-Matrix Adhesions," *Journal of Cell Science*, 2001, pp. 3583-3590, vol. 114.
Romanov, V.I., et al., "Phage Display Selection of Peptides That Affect Prostate Carcinoma Cells Attachment and Invasion," *Prostate*, 2003, pp. 239-251, vol. 47(4).
Samoylova, T.I., et al., "Targeting Peptides for Microglia Identified Via Phage Display," 2002, pp. 13-21. vol. 127(1-2).
Samoylova, T.I., et al., "Molecular Markers of Glial Tumors: Current Tarteting Strategies," *Curr. Med. Chem.*, 2003, pp. 831-843, vol. 10(10).
Gehlsen, K.R., et al., "Inhibition of In Vitro Tumor Cell Invasion by Arg-Gly-Asp-containing Synthetic Peptides," *The Journal of Cell Biology*, Mar. 1988, pp. 925-930, vol. 106.

* cited by examiner

*Primary Examiner*—Larry R. Helms
*Assistant Examiner*—David J. Blanchard
(74) *Attorney, Agent, or Firm*—Alston & Bird LLP

(57) ABSTRACT

Compositions for use in characterization, diagnosis, prognosis, and therapy of cancer cells are provided. The compositions comprise peptides and variants thereof which were isolated based on their ability to selectively bind glioma cells.

13 Claims, 11 Drawing Sheets

Selection Scheme 1
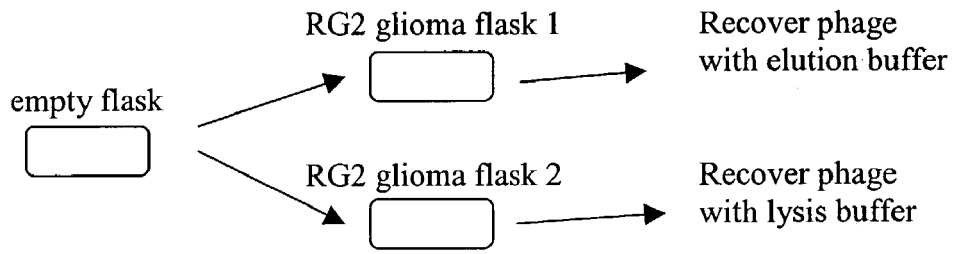
Selection Scheme 2
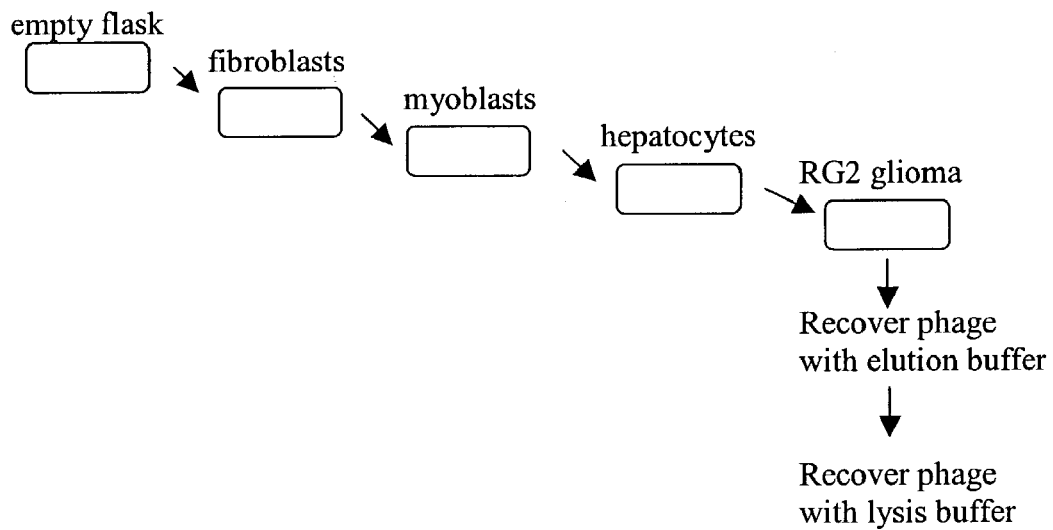
Selection Scheme 3
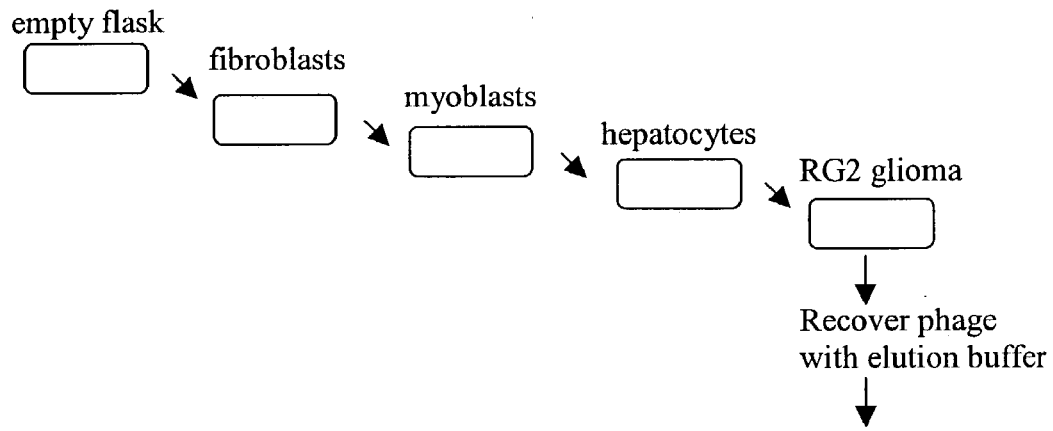
FIGURE 1

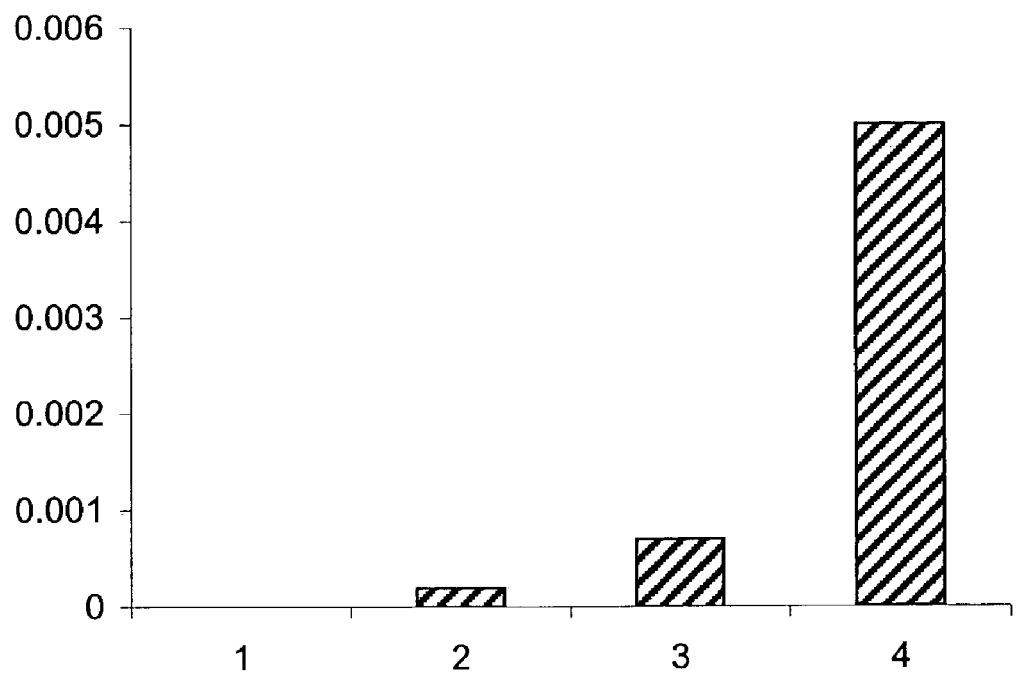
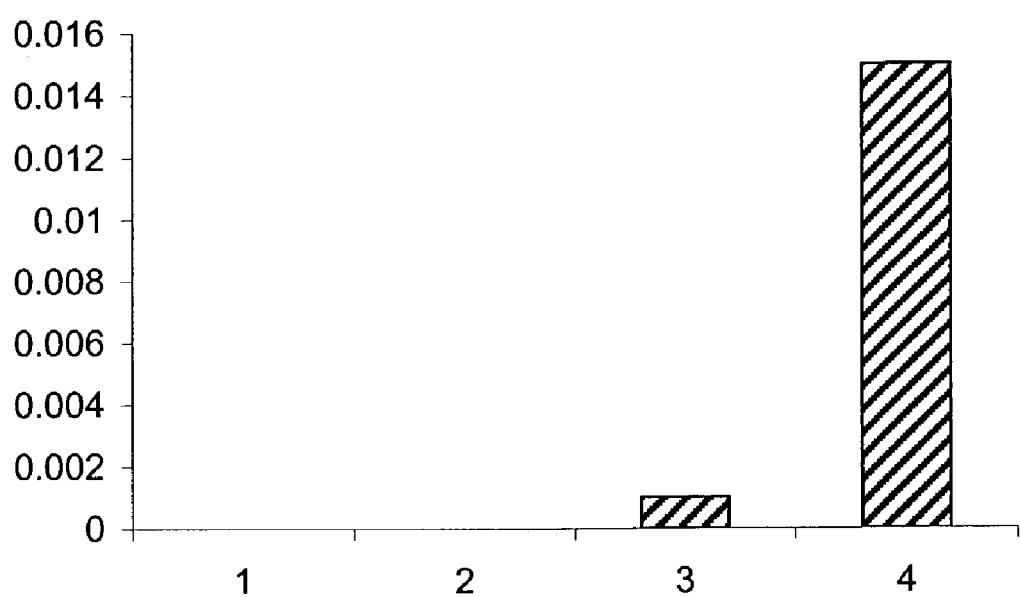
FIGURE 2

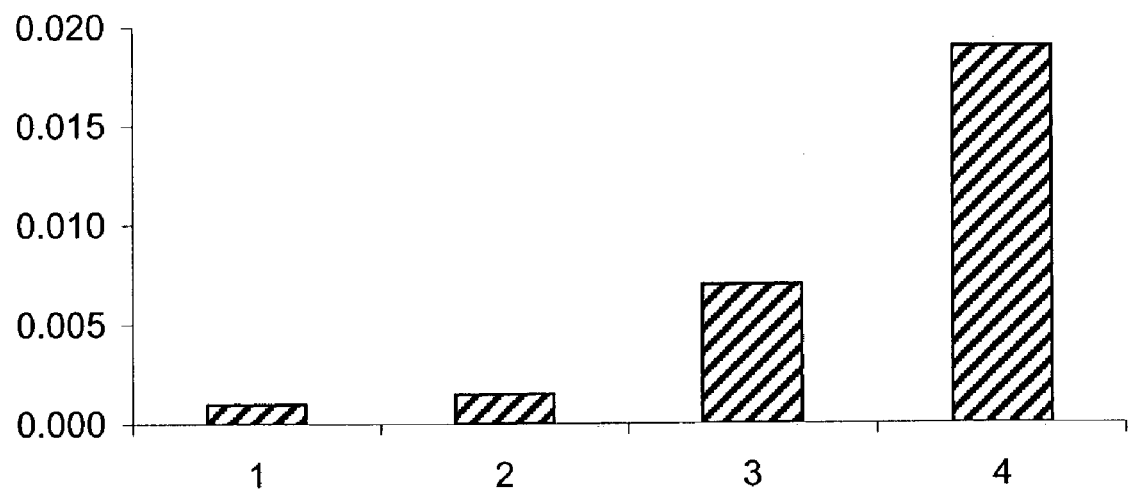
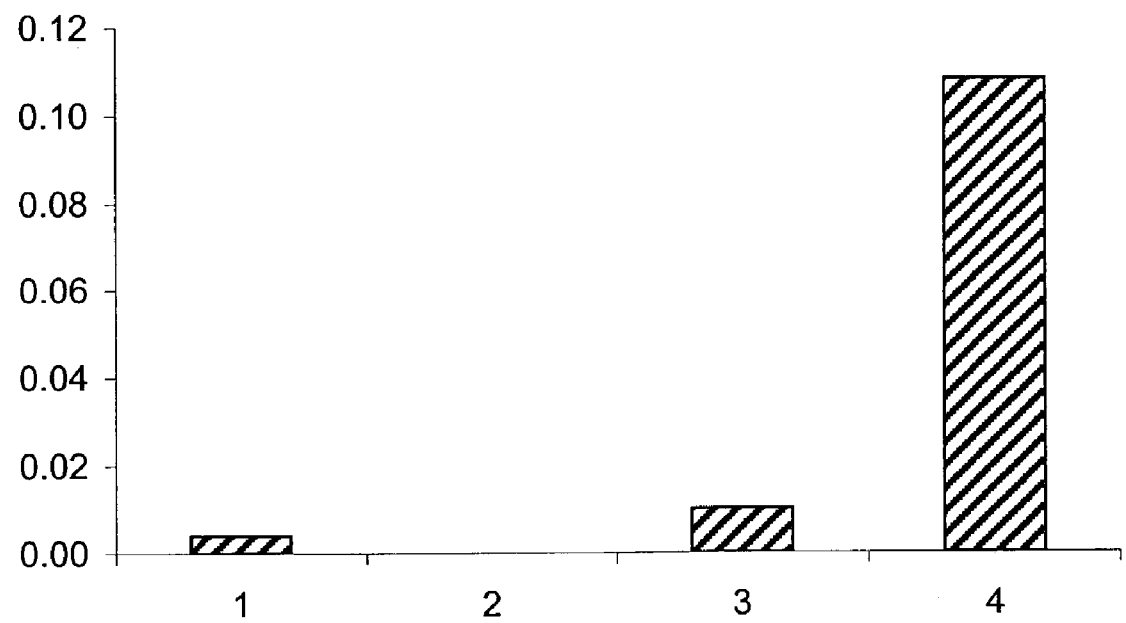
FIGURE 6

PEPTIDES FOR RECOGNITION AND TARGETING OF GLIAL CELL TUMORS

CROSS-REFERENCE TO RELATED APPLICATION

This application claims the benefit of U.S. Provisional Application No. 60/354,118, filed Feb. 4, 2002.

FIELD OF THE INVENTION

The invention relates to identification of peptides for the recognition, isolation, characterization, and targeting of glial cell tumors.

BACKGROUND OF THE INVENTION

It has been estimated that in the year 2000, approximately 350,000 people were living with a primary brain tumor (Davis et al. (2001) *Neurooncology* 3: 152–158). The expected incidence of new cases of primary brain tumors in the United States is estimated to be over 35,000 for the year 2001 (Central Brain Tumor Registry of the United States fact sheet (2001), available from CBTRUS, Chigaco, Ill.). Approximately 13,000 people die of malignant brain tumors in the United States each year, representing about 2% of all cancer deaths (Greenlee et al. (2001) *Cancer J. Clin.* 51: 15–36). Brain tumors are the second leading cause of cancer-related deaths in children under the age of 20 (Id.).

Glial tumors or gliomas are tumors which arise from neuroectodermal cells of the glial lineage and include glioblastomas (about 23% of primary brain tumors), astrocytomas (about 8% of primary brain tumors), anaplastic astrocytomas (about 4% of primary brain tumors), and oligodendrogliomas (about 3% of primary brain tumors). Of these, glioblastomas, which are malignant gliomas, are the most aggressive and difficult to treat (Roth & Weller (1999) *Cell Mol. Life Sci.* 56: 481–506; Badie & Schartner (2001) *Microsci. Res. Tech* 54: 106–113). Glioblastomas are the most common type of brain tumors in adults and by far the most devastating (Id.). While glioblastomas do not metastasize outside the brain, they are highly infiltrative and typically compress and destroy adjacent brain tissue and obstruct the flow of cerebrospinal fluid (CSF). Patients with glioblastomas are immunosuppressed both locally and systemically by a process which is poorly understood but which involves the secretion of TGF-$\beta$ and other cytokines (Roth & Weller (1999) *Cell Mol. Life Sci.* 56: 481–506).

Gliomas are poorly immunogenic, and no glioma-specific antigens have been recognized (Badie & Schartner (2001) *Microsci. Res. Tech* 54: 106–113). While the blood-brain barrier may be disrupted in some areas affected by glioma, frequently the blood-brain barrier is intact where migrating glioma cells infiltrate into normal brain tissue (Roth & Weller (1999) *Cell Mol. Life Sci.* 56: 481–506). Gliomas are very heterogeneous, varying greatly not only from individual to individual, but also in the neoplastic cell populations within a tumor (Id.). Gliomas exhibit variable expression of cell surface markers. These characteristics are major impediments for therapies designed to target tumor cells.

Current treatment of glioblastomas is multimodal (Id.; Spear et al. (1998) *J. Neurovirol.* 4: 133–137). Surgical resection is often performed to reduce tumor load and to prevent or reduce complications associated with compression. However, it is seldom possible to completely remove the tumor due to its location and/or its infiltrative growth pattern. Radiotherapy is considered to be the most effective treatment for glioblastomas, although there are several major drawbacks to this treatment: many gliomas are resistant to irradiation-induced cytotoxicity; normal brain tissue tolerance cannot be exceeded; and radiotherapy generates late side effects (Roth & Weller (1999) *Cell Mol. Life Sci.* 56: 481–506). Chemotherapy is also limited in its effectiveness because of toxic effects on normal tissues, including myelosuppression and peripheral neurotoxicity (Id). While combinations of surgery, radiotherapy, and chemotherapy are currently used to treat tumors, glioblastomas are usually fatal within one to two years of onset of symptoms (Karpati et al. (1999) *Curr. Opin. Mol. Ther.* 1: 545–552).

One desirable alternative to these conventional therapies is more specific, genetically-based therapies to allow specific targeting of tumor cells for diagnostic and prognostic tests and for therapeutic treatments. One ligand discovery approach has been to generate monoclonal antibodies against tumor cells and screen them for specificity (see, e.g., Wikstrand et al. (1999) *Cancer Metastasis Rev.* 18: 451–464). While antibody-mediated targeting of tumor cells has shown clinical promise, there are several limitations on the usefulness of antibodies. Monoclonal antibody techniques are expensive, time-consuming, and dependent on the immunogenicity of targets, a property which gliomas often lack. Monoclonal antibodies may not be useful for identification and targeting of conserved cell-specific receptors due to the receptor size, structure, and/or lack of immunogenicity. Further, antibodies are relatively large, which may limit their uptake into tumor cells, and antibodies are also taken up nonspecifically by reticulendothelial cells in non-tumor tissues (Aina et al. (2002) *Biopolymers* 66: 184–199). Although it may be possible to improve targeting of specific cells markers by further manipulation of antibodies, antibody-based methods are currently limited in their usefulness.

Thus, there remains a need for improved therapies to treat brain tumor patients as well as for more sensitive diagnostic and prognostic techniques. Molecular profiles of neoplastic cells based on DNA, mRNA, and/or protein alterations are rapidly being developed and utilized not only to augment diagnosis but to provide new therapeutic measures. Of these profiles, protein and protein-associated markers, particularly those on the tumor cell surfaces, lend themselves most readily to targeting procedures.

Protein surface markers have been described in association with malignant glioma cells. Growth factors such as EGF, PDGF, and cytokines have been exploited because they not only bind to upregulated surface receptors, but also modulate cell proliferation and differentiation. Additionally, the structures of these factors and their receptors are known, allowing for genetic and chemical manipulations to improve binding affinity, reduce immune complications, and disrupt associated molecular pathways. Growth factor receptors that have been described in association with malignancy include: epidermal growth factor receptor (EGFR; see Kuan et al. (2000) *Int. J. Cancer* 88: 962–969; Wikstrand et al. (1998) *J. Neurovirol.* 4: 148–158); platelet derived growth factor receptor (PDGFR; see Nister et al. (1987) *Cancer Res.* 47: 4953–4960; Maher et al. (2001) *Genes Dev.* 15: 1311–1333; Westermark et al. (1995) *Glia* 15: 257–263). See also, Roth & Weller (1999) *Cell Mol. Life Sci.* 56: 481–506. Surface markers include cytokine receptors such as interleukin-4 receptor (IL-4 R; see Puri et al. (1996) *Cancer Res.* 56: 5631–5637; Rahaman et al. (2002) *Cancer Res.* 62: 1103–1109) and interleukin-13 receptor (IL-13 R; see Liu et al. (2000) *Cancer Immunol. Immunother.* 49: 319–324). Surface markers also include: transferrin receptor (TfR; see Li et al. (2002) Trends Pharmacol. Sci. 23: 206–209); urokinase-type plasminogen activator receptor (uPAR; see Del Rosso et al. (2002) Clin. Exp. Metastasis 19: 193–207; Kroon et al. (2000) Blood 96: 2775–2783); chloride channels (see Soroceanu et al. (1998) Cancer Res. 58: 4871–4879; Ransom et al. (2001) J. Neurosci. 21: 7674–7683) membrane-type matrix metalloproteinases (MT-MMPs; see Fillmore et al. (2001) J. Neurooncol. 53: 187–202); cell adhesion molecules such as integrins (see Goldbrunner et al. (1999) Acta Neurochir (Wien) 141: 295–305; Tonn et al. (1998) Anticancer Res. 18: 2599–2606; Paulus et al. (1996) Lab. Investigation 75: 819–826; and Laws, Jr., et al. (1993) Int. J. Dev. Neurosci. 11: 691–697); and CD44s (see Ranuncolo et al. (2002) J. Surg. Oncol. 79: 30–35; Breyer et al. (2000) J. Neurosurg. 92: 140–149). However, the presence of these receptors on normal cells, particularly during development or wound healing, makes targeting these receptors less desirable because of possible side effects on normal tissues.

The majority of markers utilized for targeting are those that are either upregulated, resulting in increased numbers of binding sites for the targeting ligand, or are rearranged molecules, allowing glioma-selective binding when compared to normal cells. For example, Debinski et al. ((2000) J. Neurooncol. 48: 103–111) showed that an increased number of binding sites for IL-13 accompanied the progression of gliomas from low to high grade. Similarly, transferrin receptors were shown to be present in significantly greater numbers on the surface of malignant glioma cell lines when compared to normal control cell lines (Wen et al. (1993) Neurosurgery 33: 878–881). In addition to cell surface markers, naturally-occurring neuroectodermal cell-specific ligands such as chlorotoxin (ClTx), a 4-kilodalton peptide from the venom of scorpions, have been used as targeting molecules for gliomas (Soroceanu et al. (1998) Cancer Res. 58: 4871–4879; Lyons et al. (2002) Glia 39: 162–173). The chlorotoxin peptide shows high-affinity, specific binding to glioma cells and may find use in therapeutic and diagnostic applications.

One of the few unique markers to tumor cells is a frequently rearranged form of EGFR known as EGFR type III variant ("EGFRvIII"), also called "de2-7 EGFR" (Johns et al. (2002) Int. J. Cancer 98: 398–408). This marker has a deletion in the extracellular domain, resulting in a tumor-specific cell surface receptor that is found on a variety of tumor cell types including malignant glioma, breast carcinoma, non-small cell lung carcinomas, and ovarian tumors (Kuan et al. (2001) Endocr. Relat. Cancer 8: 83–96).

With the exception of the rearranged EGFRvIII and IL-4-independent IL-13Rα2 (see, e.g., Nagane et al. (2001) J. Neurosurg. 95: 472–492), the surface molecules described above also are expressed by normal cells, limiting their usefulness in diagnosis or therapy. Additionally, there is frequently variation in marker expression within the same tumor mass over time with neoplastic progression or among the same type of tumors from different individuals. The multifunctional adhesion molecule involved in cell—cell and cell-matrix interactions, CD44s, was shown to be differentially expressed such that low-grade astrocytomas (9.5%) had far fewer cells with high expression of CD44s than did glioblastomas (59%), while positive CD44s staining was heterogeneous even within samples (Ranuncolo et al. (2002) J. Surg. Oncol. 79: 30–35). Such intratumoral and intertumoral heterogeneity of tumor cells indicates that no single marker will be able to provide diagnosis and/or targeting for all gliomas, but instead that an array of markers will be necessary for such purposes.

Small peptides that bind to cell surface markers also have been utilized in targeting strategies. The advantages of peptide ligands are their small size, specificity, and chemical stability, the ease with which they can be derivatized, and their general lack of binding to reticuloendothelial cells, in contrast to antibodies (Aina et al. (2002) Biopolymers 66: 184–199). Spear et al. ((2001) Cancer Gene Ther. 8: 506–511) used phage display technology to identify cell surface biorecognition molecules for brain tumors using different human and rat cell lines. However, the phage clones identified were found to have low binding specificity for glioma cells based on evaluations using ELISA. Thus, while some peptide ligands have been identified, there remains a need for additional peptide ligands which will preferentially bind to gliomas for use in diagnosis, prognosis, and therapy.

SUMMARY OF THE INVENTION

Compositions and methods for targeting nucleic acids, proteins, pharmaceuticals, or other compounds to cells of glial cell tumors are provided. The compositions comprise peptide sequences which bind to cells of glial cell tumors with high specificity.

The compositions are useful in characterization, diagnosis, prognosis, and therapy of gliomas, and also are useful for delivery of a wide variety of compounds to the cells of glial cell tumors, including nucleotides, proteins (including, for example, toxins), liposomes, and small molecule pharmaceuticals. The compositions are also useful in identifying cell surface markers to which the compositions bind.

BRIEF DESCRIPTION OF THE DRAWINGS

FIG. 1 shows selection schemes for identification of phage clones that recognize molecular markers on RG2 glioma cells. For each Selection Scheme, only the first round of selection is shown in the Figure. The consecutive rounds were performed in the same manner in all three schemes, as described in Experimental Example 1.

In Selection Scheme 1, RG2 cells were grown to a sub-confluent monolayer. First, an aliquot of the primary library in washing/blocking buffer was added to an empty flask (depletion flask) to remove plastic-binding phage clones. The library aliquot contained approximately 100 copies of each phage clone. The buffer containing the depleted aliquot (i.e., phage that did not bind to plastic) was transferred to two flasks with RG2 glioma cells for incubation. After incubation, unbound phage were removed by washing. Tumor cell-surface-bound phage were recovered with low-pH elution buffer ("RG2 glioma flask 1" of FIG. 1). In a parallel experiment ("RG2 glioma flask 2" of FIG. 1), all phage clones, including both cell-surface bound and internalized phage, were recovered using lysis buffer. Phage from the elution buffer fraction and phage from the lysis buffer fraction were amplified in bacteria and used in subsequent rounds of selection for tumor cell binding.

In Selection Scheme 2 (FIG. 1), the library aliquot contained approximately 100 copies of each phage clone. Prior to incubation with RG2 cells, a depletion or negative selection step was performed with fibroblasts, myoblasts, and hepatocytes to remove phage that bound to these normal cells. Phage associated with RG2 cells were recovered from a single flask in two sequential steps, first with elution buffer and then with lysis buffer.

In Selection Scheme 3 (FIG. 1), the library aliquot contained approximately 10 copies of each phage clone (i.e., ten-fold less of the primary library was used in comparison to Selection Schemes 1 and 2). Also, blocking phage was added to the library aliquot and astrocytes were included as a cell type in the depletion or negative selection steps.

FIG. 2 shows enrichment in the yield of cell-associated phage obtained using Selection Scheme 1 followed by consecutive selection rounds on RG2 glioma cells. After the depletion step, RG2 cells were incubated with the remaining pool of primary phage display library. Unbound phage were washed away and then either (a) cell-membrane bound phage were recovered with elution buffer (see FIG. 1, "RG2 glioma flask 1") or (b) phage associated with the cells (including cell membrane-bound and internalized phage) were recovered with lysis buffer (see FIG. 1, "RG2 glioma flask 2"). Both the elution buffer phage fraction and the lysis buffer phage fraction were amplified in bacteria and used in the next selection round. The charts in FIG. 2 show the ratio of output to input phage (vertical axis) for each round of selection (horizontal axis). The upper graph in the figure shows results obtained using the elution buffer phage fraction, and the lower graph shows results obtained using the lysis buffer phage fraction. Each chart shows results from four rounds of selection.

Figure 3:
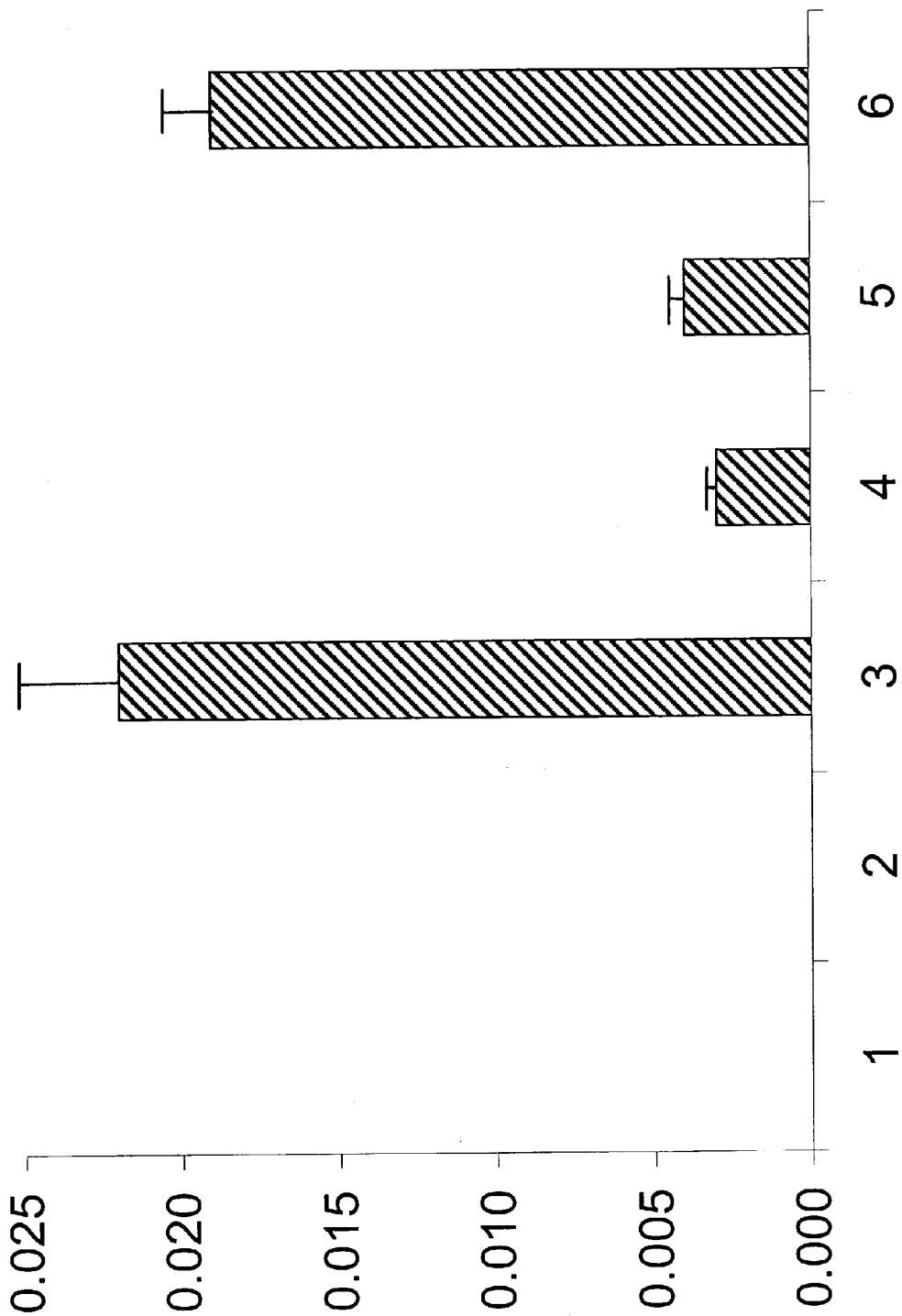

FIG. 3 shows the binding of affinity-selected and control phage clones to RG2 glioma cells after selection using Selection Scheme 1. RG2 cells were grown to sub-confluent monolayers and incubated with different pure phage clones selected for their ability to bind RG2 cells (clones 3 (designated #3 on graph), 12 (#4), 15 (#5), and 19 (#6)) and contral phage clones (1F20 (#1 on graph) and f8-5 (#2 on graph)). Subsequently, unbound phage were washed away and attached (i.e., cell-membrane-bound) phage were eluted from cell surfaces with low pH buffer. Phage titers for output and input phage were determined by infection of bacteria; the chart shown in FIG. 3 represents the ratio of output to input phage (vertical axis) for each phage clone (horizontal axis). Data represent the mean+/−SD of analyses performed in triplicate. The numbers for control phage were too low to be seen in the chart. The sequences of synthetic peptides displayed by the affinity-selected phage clones used in these experiments were: clone 3, VGLPEHTQ (SEQ ID NO: 9); clone 12, VDLPTHSS (SEQ ID NO:4); clone 15, VDLPEHGK (SEQ ID NO:1); and clone 19, VDLPQHGQ (SEQ ID NO: 10).

Figure 4:
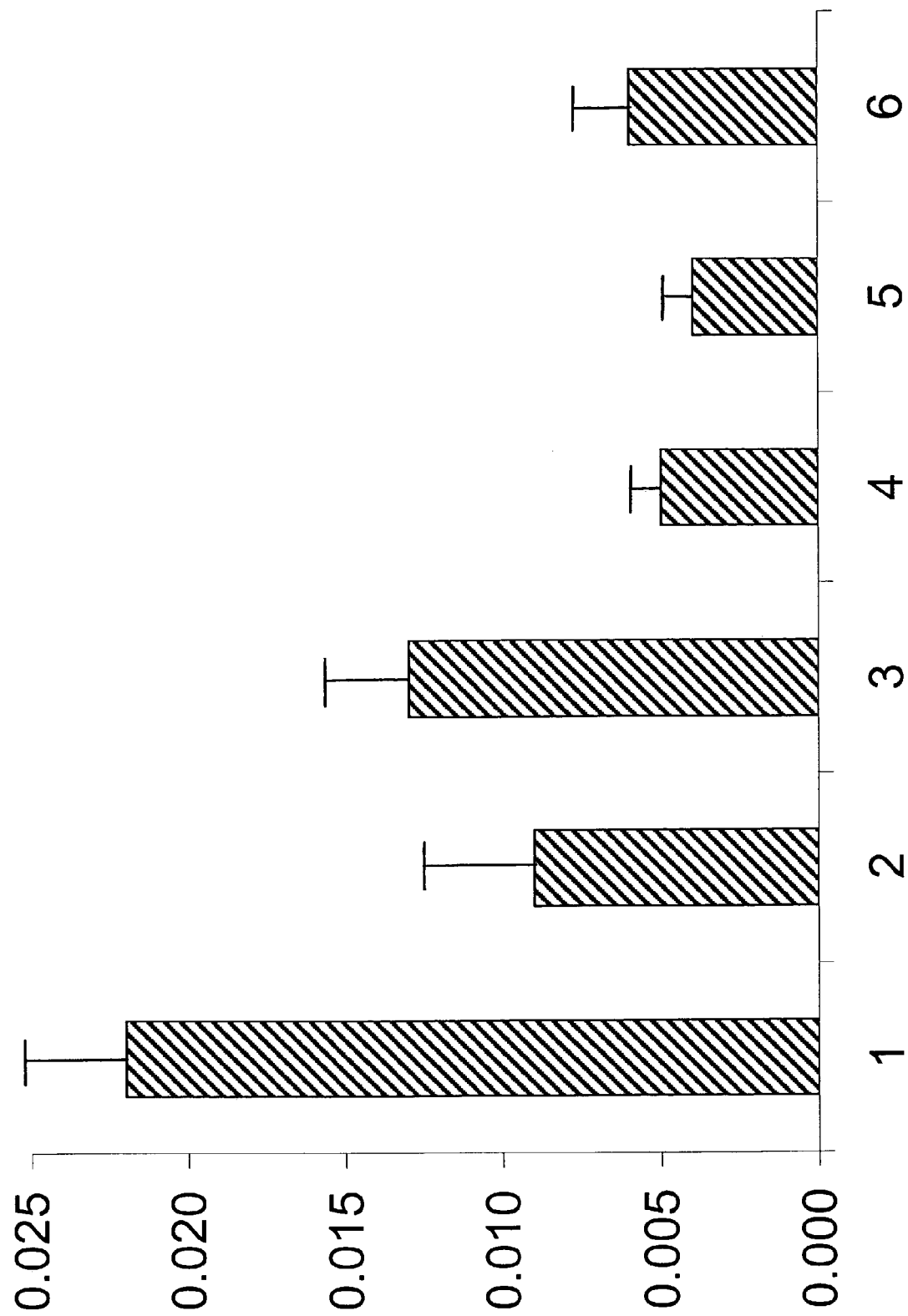

FIG. 4 shows the binding of the glioma-specific VGLPEHTQ (SEQ ID NO: 9) phage clone (i.e., the phage clone displaying the synthetic peptide VGLPEHTQ) to RG2 and control cells after selection of phage with Selection Scheme 1. RG2 glioma and control cells which included F98 glioma, astrocytes, myoblasts, fibroblasts, and hepatocytes were incubated with the phage clone bearing the VGLPEHTQ peptide. After incubation, unbound phage were removed and phage attached to the cells were eluted with low-pH elution buffer. Phage titers in the eluates were determined and plotted in FIG. 4 as output to input phage ratios (vertical axis) for each cell type (horizontal axis). On the horizontal axis, the cell types tested are indicated as follows: 1, RG2 glioma; 2, F98 glioma; 3, astrocytes; 4, myoblasts; 5, hepatocytes; and 6, fibroblasts (for details, see Experimental Example 1).

Figure 5:
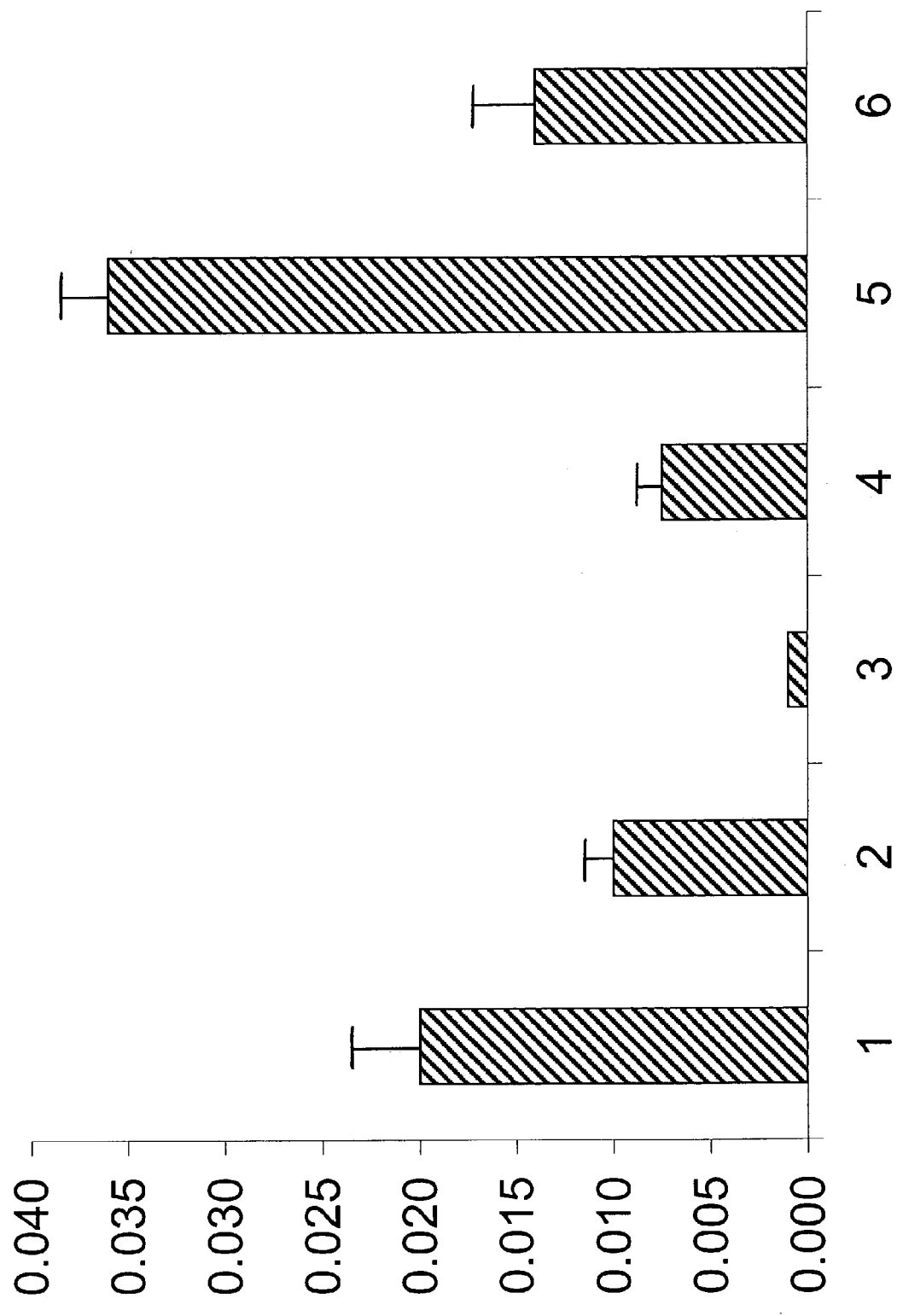

FIG. 5 shows the selectivity of the ELRGDSLP (SEQ ID NO:12) phage clone binding to RG2 glioma cells compared to control cells. The ELRGDSLP phage clone was selected using Selection Scheme 1 and was recovered by lysis after incubation with cells of all types, including RG2 and control cells as shown in the Figure. Phage associated with each cell type are presented as the ratios of output to input phage for each cell type. On the horizontal axis, the cell types tested are indicated as follows: 1, RG2 glioma; 2, F98 glioma; 3, astrocytes; 4, myoblasts; 5, hepatocytes; and 6, fibroblasts (for details, see Experimental Example 1).

FIG. 6 shows the enrichment in cell-associated phage in consecutive selection rounds on RG2 glioma cells obtained after using Selection Scheme 2 (see Experimental Example 1). The phage display library was subjected to several depletion or negative selection steps in the first round, after which phage display library was added to a flask with RG2 glioma cells for incubation. Subsequently, unbound phage were removed by washing and the rest of the phage were recovered from cells in sequential steps by elution with low pH buffer ("elution buffer" fraction, shown in upper graph) and then by cell lysis ("lysis buffer" fraction, shown in lower graph). Both phage fractions were amplified in bacteria and used in further rounds of affinity selection. The data shown in the figures represent the ratio of output to input phage for each round of selection for each phage fraction.

Figure 7:
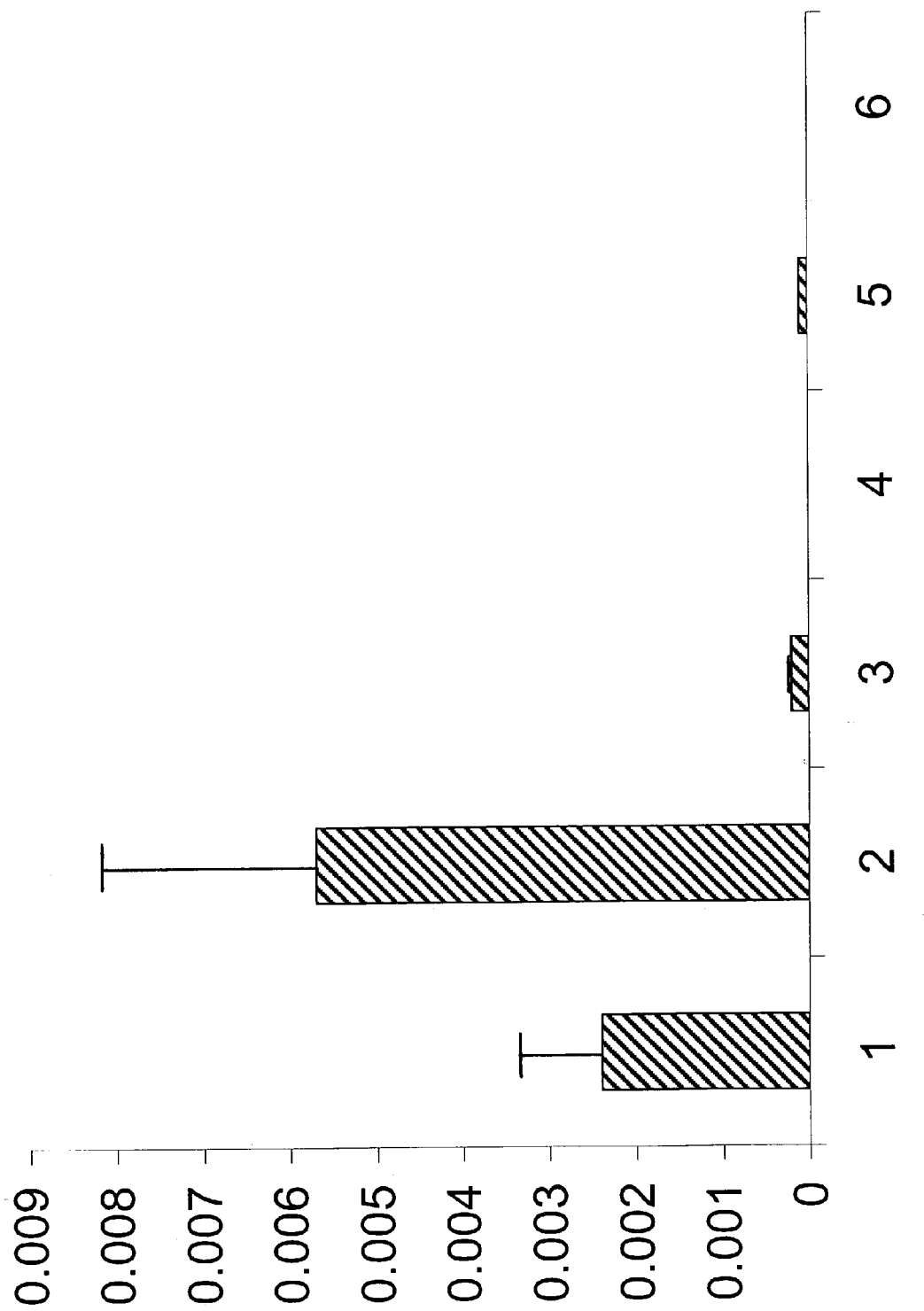

FIG. 7 shows binding of the DSTKSGNM (SEQ ID NO:28) phage clone to RG2 glioma and control cells. This phage clone was isolated from the elution buffer fraction of a library screened with Selection Scheme 2. RG2 glioma and control cells were incubated with the DSTKSGNM phage clone. Phage attached to the cells were recovered by elution. Phage titers in the eluates were determined and plotted as output to input ratios (vertical axis) for each cell type (horizontal axis). On the horizontal axis, the cell types tested are indicated as follows: 1, RG2 glioma; 2, F98 glioma; 3, astrocytes; 4, myoblasts; 5, hepatocytes; and 6, fibroblasts.

Figure 8:
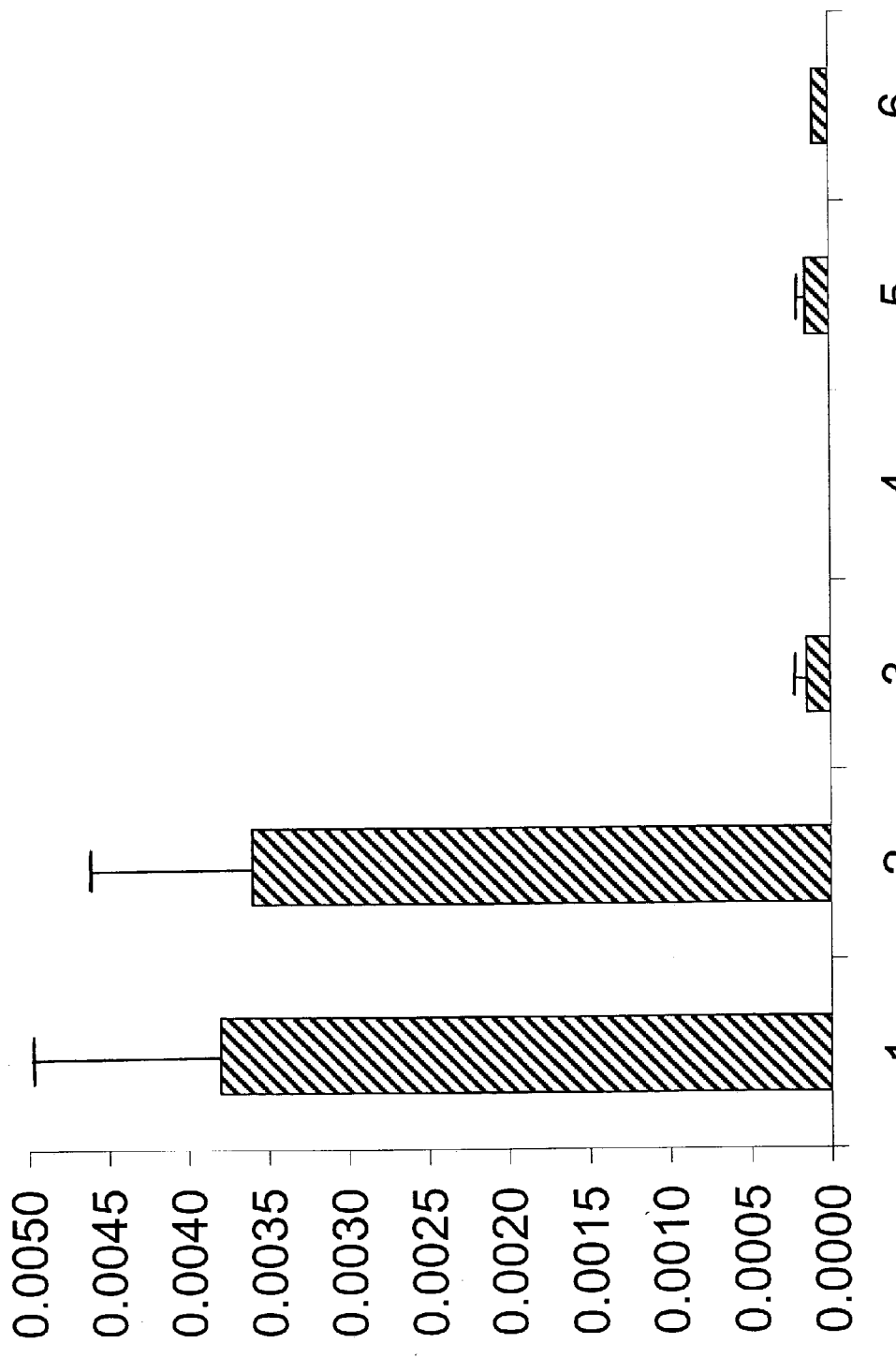

FIG. 8 shows the selectivity of DYDMTKNT (SEQ ID NO:39) phage clone binding to RG2 glioma compared to control cells. This phage clone was isolated from the lysis buffer fraction of a library screened with Selection Scheme 2. After incubation with DYDMTKNT phage, cells were lysed and cell-associated phage were recovered (see Experimental Example 1). Titer of phage in cell cultures of all cell types were determine by infection of bacteria. Phage titers in the eluates were determined and plotted as output to input ratios (vertical axis) for each cell type (horizontal axis). On the horizontal axis, the cell types tested are indicated as follows: 1, RG2 glioma; 2, F98 glioma; 3, astrocytes; 4, myoblasts; 5, hepatocytes; and 6, fibroblasts.

Figure 9:
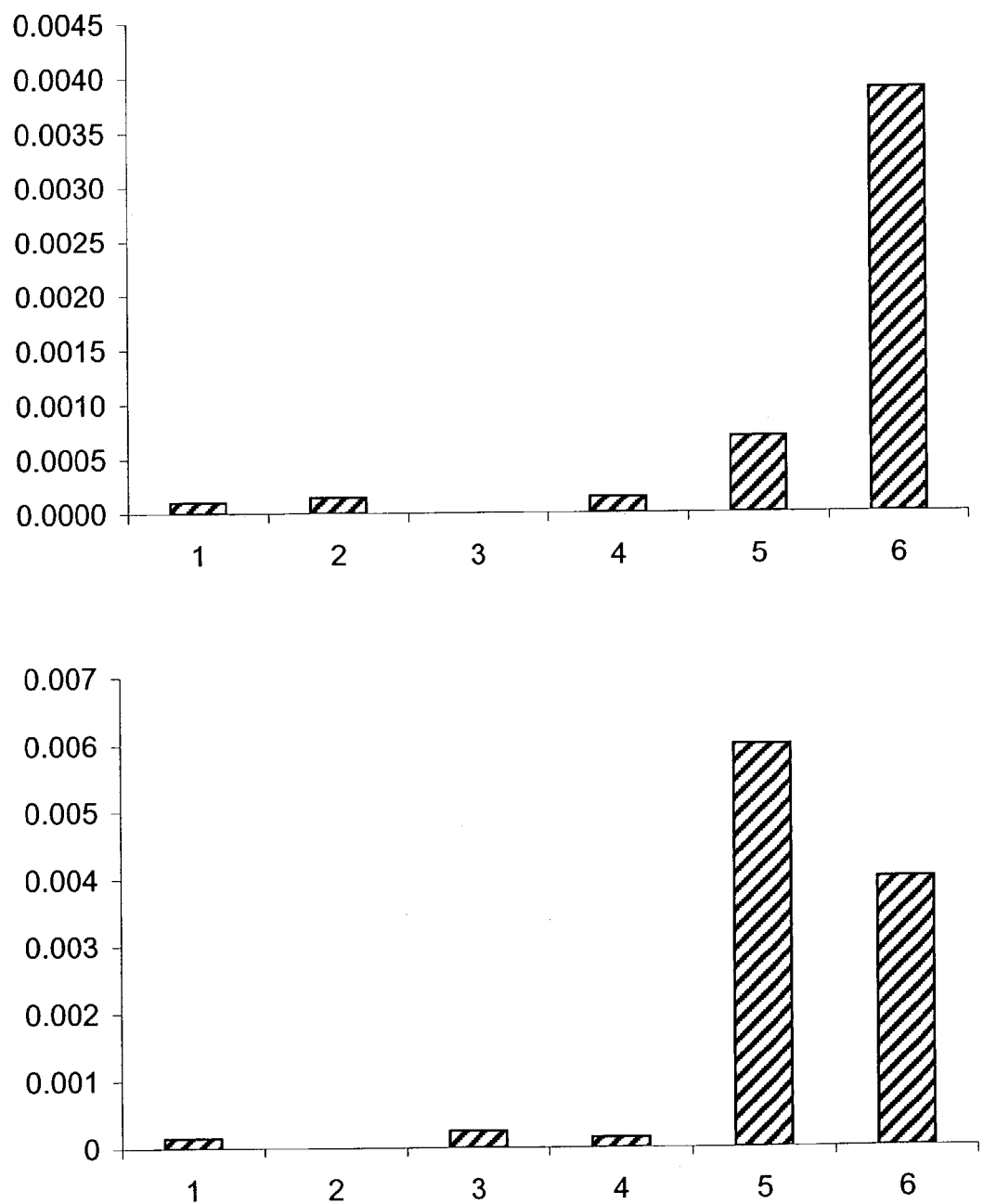

FIG. 9 shows enrichment in cell-associated phage in six rounds of selection on RG2 glioma cells after using Selection Scheme 3. Selection Scheme 3 is similar to Selection Scheme 2, with the following changes in the first round: (1) ten-fold less of the primary library was applied to cells; (2) blocking phage was added to the incubation buffer; and (3) astrocytes were used in place of fibroblasts for negative selection. In all, six rounds of selection were performed. For each round, the ratio of output to input phage was calculated; results are shown in the upper graph for the "elution buffer" fraction and in the lower graph for the "lysis buffer" fraction.

Figure 10:
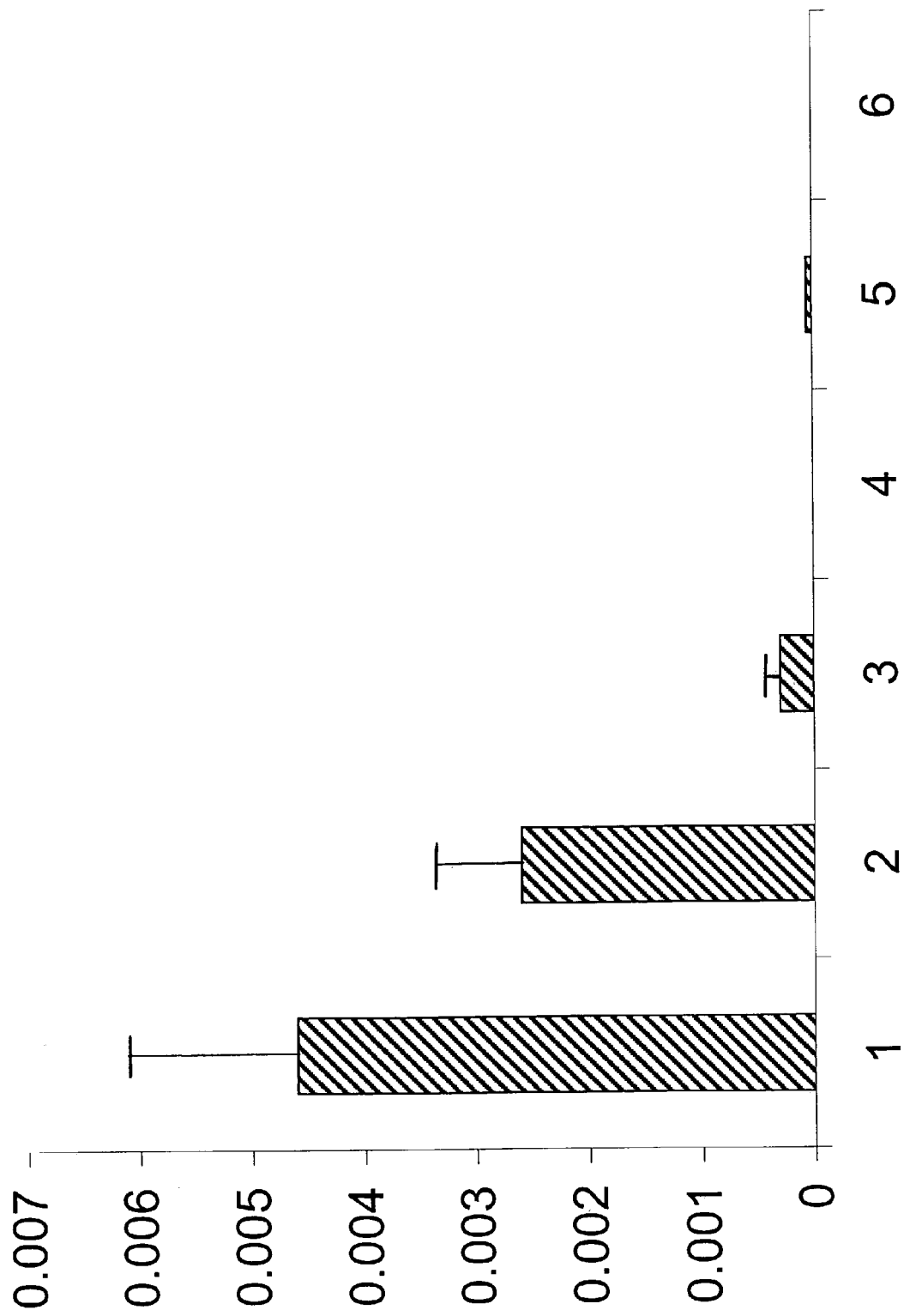

FIG. 10 shows binding of the DLTKSTAP (SEQ ID NO:43) phage clone to RG2 glioma and control cells. This clone was isolated from the elution buffer fraction after a screen of a phage library using Selection Scheme 3. For binding analysis, RG2 glioma and control cells were incubated with the DLTKSTAP phage clone and phage attached to the cells were recovered by elution. Phage titers in the eluates were determined and plotted as output to input ratios (vertical axis) against different cell types (horizontal axis). On the horizontal axis, the cell types tested are indicated as follows: 1, RG2 glioma; 2, F98 glioma; 3, astrocytes; 4, myoblasts; 5, hepatocytes; and 6, fibroblasts.

Figure 11:
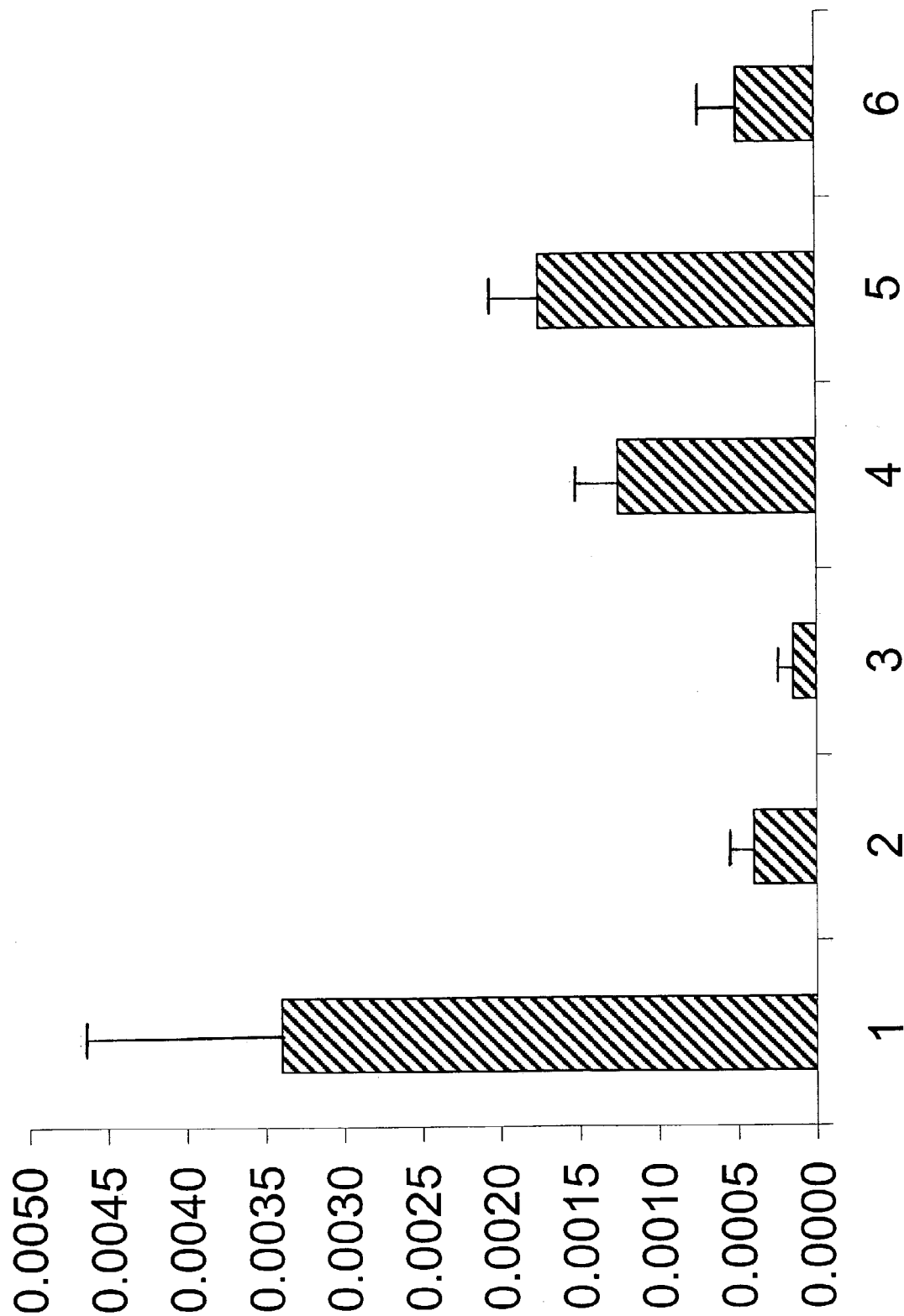

FIG. 11 shows selectivity of ESRGDSYA (SEQ ID NO:46) phage clone to RG2 glioma and control cells. This clone was isolated from the lysis buffer fraction after a screen of a phage library using Selection Scheme 3. For binding analysis, aliquots of the ESRGDSYA phage clone was incubated with cells; the cells were lysed and cell-associated phage were recovered (see Experimental Example 1). Titer of phage in cell cultures of all cell types were determined by infection of bacteria. Phage titers in the lysates were plotted as output to input ratios (vertical axis) for each cell type (horizontal axis). On the horizontal axis, the cell types tested are indicated as follows: 1, RG2 glioma; 2, F98 glioma; 3, astrocytes; 4, myoblasts; 5, hepatocytes; and 6, fibroblasts.

DETAILED DESCRIPTION OF THE INVENTION

Targeting of tumor cells for diagnostic and prognostic imaging techniques, immunotherapy, transfection of cells for gene therapy, and cell-specific drug therapy all require targeting specificity.

The present invention provides compositions that can be used to characterize a particular cell population as well as to deliver compounds to that cell population. Delivery may occur by bringing a compound into the vicinity of the target cells, such as to the cell surface, or delivery may capitalize on endogenous cellular pathways of macromolecular transport such that compounds are internalized within the target cells. In this manner, delivery of compounds may be accomplished via the receptor-mediated endocytosis pathway employing molecular conjugate vectors.

The invention is drawn to peptides that have been shown to bind glioma cells or to bind to glioma cells with high specificity. Further provided are nucleic acids comprising nucleotide sequences that encode the peptides of the invention, and vectors comprising these nucleic acids. The peptides are useful for targeting compounds to glioma cells for diagnostic, prognostic, and/or therapeutic purposes. Such compounds include labeling compounds used for cytology or histology, pharmaceuticals, proteins (including, for example, toxins), liposomes, and genetic material such as, for example, DNA. In this manner, the peptides of the invention may be used to effect gene transfer into target cells in vivo and may also be used with tissue samples in vitro and/or in situ for diagnostic and/or prognostic purposes. While the peptides of the invention have been selected based on their ability to bind glioma cells, it is understood that these peptide sequences may also bind to other tumor cells that are not glioma cells. In this manner, the peptides of the invention may also be useful in diagnosis and/or therapy of non-glioma tumors, or may be useful in comparing various cell populations based on cell surface marker characteristics. For example, peptides containing the motif $V_{(D/G)}LP_{(E/T)}H$ (SEQ ID NO:8) bound to all cell types tested and therefore probably binds to a common cell surface marker. Peptides containing this motif can be useful in the isolation and identification of a cell surface marker which may be a novel receptor (see, e.g., Experimental Example 2) and also can be useful in assays comparing various cell types for expression of cell surface markers.

The peptides of the invention are generally short peptide ligands, and are referred to herein as "synthetic peptides" or "peptides." The synthetic peptides of the invention may exhibit at least two-fold, three-fold, four-fold, five-fold, six-fold, seven-fold, ten-fold, twenty-fold, thirty-fold or more increased binding affinity for glioma cells relative to at least one category or type of other cells. Synthetic peptides that exhibit such binding characteristics are said to exhibit preferential binding to glioma cells. Synthetic peptides that do not exhibit at least a two-fold increased binding affinity for glioma cells relative to another category or type of other cells but that bind to glioma cells are simply said to bind to glioma cells.

The synthetic peptides of the invention are cell-binding and cell-entry peptides. For the most part, these synthetic peptides will comprise at least about 5 to about 50 amino acids, preferably at least about 5 to about 30 amino acids, more preferably at least about 6, 7, 8, 9, 10, 11, 12, 13, 14, 15, 16, 17, 18, 19, or up to about 20 amino acids. It is recognized that motifs or sequence patterns may be identified among the peptides that are capable of binding to a target. Such motifs identify key amino acids or patterns of amino acids that are essential for binding. Motifs may be determined from an analysis of peptide patterns that are capable of binding glioma cells (see, e.g., Experimental Example 1 and SEQ ID NOs: 8, 40, 41, 42, 51, 53, and 54). Such motifs may be as short as 3 amino acids in length, or they may be 4, 5, 6, 7, 8, 9, 10, 11, 12, 13, 14, 15, 16, 17, 18, 19, or 20 amino acids in length. Motifs can contain amino acid residues which are invariant as well as amino acid residues which may be substituted by one or more other amino acids without affecting the properties conferred by the motif. For example, the $D_{(T/S/L/M)}TK$ motif (SEQ ID NO:52) contains invariant amino acids as the first (D), third (T), and fourth (K) amino acid in the motif, while also containing one of the amino acids T, S, L, or M as the second amino acid in the motif. Thus, this motif includes the sequences DTTK, DSTK, DLTK, and DMTK.

Once identified, these motifs can be used in constructing other peptides for use in targeting cell populations. Motifs may be evaluated by constructing peptides containing the motif and determining the effect of the motif on the peptide's binding properties. It will be appreciated that the creation of variant sequences by the addition of extra copies of the same motif and/or different motifs and/or the addition of other flanking amino acids may enhance the binding properties conferred by a motif on a peptide comprising it. By "enhancing the binding properties" is intended that a peptide shows an increase in desired binding properties or a decrease in undesired binding properties. One of skill in the art can determine appropriate desired or undesired binding properties based on the particular application. For example, a peptide with enhanced binding properties may show increased binding to glioma cells compared to another particular cell type, or it may show increased binding to all cell types tested.

One of skill in the art is familiar with techniques to make and test such peptides, for example, as taught herein with appropriate modifications which would be routine to those of skill in the art. Such variant peptides are encompassed by the term "peptide" and "synthetic peptide" as used herein. The synthetic peptides can be classified into linear, cyclic and conformational types. While the invention is not bound by any particular mode of action, it is postulated that shorter peptides, which are generally from about 7 to about 20 amino acids, are involved in linear binding to the target cells. Longer peptides are thought to assume conformational folding and are involved in conformational binding. Cyclic peptide structures can also be constructed for use in the invention. In this manner, a core peptide region such as a motif sequence will be flanked with identical sequences to form cyclic peptides. For such construction, libraries are available commercially. See, for example, the Ph.D.™ phage display peptide library kits from New England Biolabs, Inc. See also, Parmley et al.(1988) *Gene* 73:305–318; Cortese et al.(1995) *Curr. Opin. Biotechnol* 6:73–80; Noren (1996) *NEB Transcript* 8(1):1–5; and Devlin et al.(1990) *Science* 249:404–406.

While the synthetic peptides of the invention were isolated based on a screen for their ability to preferentially bind RG2 glioma cells, it is expected that these peptides will also preferentially bind to other glioma cells and to glioma cells of other mammals, such as, for example, human patients. Gliomas occur in mammalian species of interest, including but not limited to human, rat, dog, mouse, cat, non-human primate, and the like. It is further understood that while the synthetic peptides of the invention were isolated for their ability to bind glioma cells, some of these peptides may also bind to other tumor cells and thus may be useful in diagnosis and targeting of other non-glioma tumors. Peptides may also bind to particular cell types, such as cell types of a particular origin. Thus, the peptides of the invention find use where they preferentially bind at least one target cell population when compared to their binding of at least one non-target-cell population such as, for example, normal astrocytes. Peptides also may bind generally to most cell types; such peptides find use, for example, in applications such as isolation and identification of novel cell surface markers and in characterization of the cell surface markers of particular cell populations.

Peptides of the invention were identified and isolated using phage display libraries in particular screening procedures, or "Selection Schemes," which are more particularly described in Experimental Example 1. Briefly, phage display libraries were created that express random synthetic peptides on the surface of each phage. Thus, the binding properties of each phage in the library are expected to reflect the binding properties of the synthetic peptide expressed on the phage surface. These phage libraries were then subjected to at least one depletion or negative selection step to remove phage that bound to the plastic used in tissue culture flasks, etc. In some Selection Schemes, the phage libraries were also subjected to depletion or negative selection steps to remove phage that bound to other cell lines such as, for example, normal astrocytes or fibroblasts. These phage libraries were then incubated with glioma cells to allow the phage to bind to and/or become internalized within the glioma cells. These affinity-selected phage were then recovered, and some of these phage were then individually isolated. The nucleotide sequence encoding the synthetic peptide for each phage clone was determined. Individual phage clones were further assayed to evaluate the binding properties conferred by the synthetic peptide. It is understood that in this context, "synthetic peptide" means a peptide that was introduced into the phage genome by engineering and is not a native phage sequence in its native context. However, because these "synthetic peptides" show binding or preferential binding to gliomas, it is expected that at least some of the synthetic peptides contain sequences and/or motifs that are found in native mammalian proteins or that share similar three-dimensional properties with native mammalian proteins.

Thus, as used herein, "synthetic peptide" refers to a peptide which has an amino acid sequence which is not a native sequence or is not in its native context and which confers on phage displaying it the ability to bind or preferentially bind to a particular cell population. By "not in its native context" is intended that the peptide is substantially or essentially free of amino acid sequences that naturally flank the amino acid sequence of the peptide in the native protein which comprises the amino acid sequence of the peptide. For example, a synthetic peptide which has a native amino acid sequence in various embodiments may be flanked at either or both ends by 1, 2, 3, 4, 5, 6, 7, 8, 9, 10, 11, 12, 13, 14, 15, 16, 17, 18, 19, 20, 25, 30, 35, 40, 45, or 50 or more amino acids found in the native protein flanking the amino acid sequence that is the same sequence as the synthetic peptide sequence.

Peptides of the invention can be determined which are capable of binding glioma cells of any origin. Based on the selective binding protocols or Selection Schemes (diagrammed in FIG. 1), peptides which are specific for glioma cells can be identified and their amino acid sequences determined. These sequences may be used to identify a motif for binding to the target cells of interest. Tables 1, 2, and 3 set forth the amino acid sequences of peptides which were identified from the Selection Schemes; many of these display preferential binding to glioma cells (see also Experimental Example 1). Thus, it will be appreciated that Selection Schemes may be varied so that negative selection or depletion may be performed against readily available CNS (central nervous system) cell lines from any mammal. Peptides can also be selected against tissue or cell preparations enriched for specific glioma cell types.

Further provided by the present invention is the array of peptides described herein which show binding or preferential binding to glioma cells. Such an array provides a molecular profile of glioma cells and thus serves to further describe and characterize glioma cells and glioma cell surfaces. In particular, the present array of peptides provides a molecular profile of the model glioma cell line RG2, a rodent model of human glioma.

The present invention also provides nucleic acids comprising nucleotide sequences that encode these peptides. One of skill in the art, given the amino acid sequence of the invention, can readily design and synthesize a nucleic acid comprising a nucleotide sequence that would encode that peptide. Further, because the synthetic peptides of the invention are relatively short, only a relatively small number of nucleotide sequences will encode the particular peptide in question.

In this study, the binding properties of affinity-selected peptides were evaluated by titering cell-associated phage. For general methods, see *Phage Display: A Laboratory Manual* (Cold Spring Harbor Laboratory Press, Cold Spring Harbor, N.Y. (2001)). Binding specificity of phage was confirmed by counting cell-associated phage following the incubation of individual phage clones with glioma cells. It was demonstrated that some affinity-selected phage are highly specific and preferentially bind to two different glioma cell lines (RG2 and F98) by several orders of magnitude compared to phage clones bearing irrelevant peptides (library vector f8-5, or clone 1F20) (see, e.g., FIG. 3).

Identified peptides were also tested for selectivity of binding to different cell types. One family of peptides was identified using Selection Scheme 1 with no negative selection or depletion step involving other cell types (see diagram in FIG. 1). This family included phage clones displaying synthetic peptides comprising the $V_{(D/G)}LP_{(E/T)}H$ binding motif (SEQ ID NO:8); this motif includes the sequences VDLPEH, VGLPEH, VDLPTH, and VGLPTH. Phage displaying these synthetic peptides bound to RG2 glioma cells but showed insignificant preferential binding to RG2 glioma cells compared to normal cells, including astrocytes and several other cell types of non-brain origin (see, e.g., FIG. 4).

Another family of synthetic peptides conferring the property of selective binding to glioma cells was those peptides comprising the $D_{(T/S/L/M)}TK$ motif (SEQ ID NO:52). Phage clones bearing peptides with this motif were isolated from Selection Schemes 2 and 3, which included negative selection or depletion steps using normal cell types prior to selection of phage for binding to RG2 cells. Two phage clones from this family were examined for cell type selectivity and were found to have the motif at the amino terminal end of the synthetic peptide sequence, while a third clone contained the motif in the middle of the synthetic peptide sequence (DYDMTKNT). Since each of these phage clones exhibited a separate binding pattern, it is unclear if all members of this family recognize the same cell surface marker. However, the observed variability in binding may be due to the different flanking sequences surrounding the consensus sequence. However, each phage clone showed preferential binding to glioma cells when compared to normal cells of brain and other tissues.

A third family of synthetic peptides was isolated from phage in cell lysates following the glioma affinity-selection step in Selection Schemes 1 and 3. This family includes synthetic peptides with the $E_{(L/V/S)}RGDS$ motif (SEQ ID NO: 54); this motif includes the sequences ELRGDS, EVRGDS, and ESRGDS. All peptides within this family contain the RGD motif that is known to bind to and various integrins. For example, the synthetic peptide ELRGDSLP (SEQ ID NO: 12) was displayed by a phage clone isolated from whole cell lysate using Selection Scheme 1. Phage clones displaying this peptide were internalized by RG2 glioma cells about 63-fold more efficiently than they were by astrocytes (see FIG. 5). Thus, the ELRGDSLP peptide might be useful in a gene therapy vector for intratumoral delivery of therapeutic genes. However, phage clones displaying the ELRGDSLP peptide showed no binding selectivity to RG2 cells in comparison to the other cell types tested, namely hepatocytes, myoblasts and fibroblasts (see FIG. 5). This lack of selectivity might be due to the expression in many tissues of different receptors known to bind the motif "RGD," such as integrins (see, e.g., Ruoslahti (1997) *Kidney Int.* 51: 1413–1417; Akiyama (1996) *Hum. Cell* 9: 181–186).

Methods are available in the art for the determination of the peptides of the invention. Such methods include selection from a bacteriophage library which expresses random peptides, mirror image phage display to isolate naturally-occurring L-enantiomers in a peptide library, and the like. See, for example, Barry et al.(1996) *Nature Medicine* 2:299–305; Schumacher et al.(1996) *Science* 271:1854–1857; Pasqualini et al.(1996) *Nature* 380:364–366; and the references cited therein, herein incorporated by reference.

Protocols to select for small peptides that will bind to tumor cells have utilized combinatorial library methods such as phage display and one-bead one-compound combinatorial peptide libraries (reviewed by Aina et al. (2002) *Biopolymers* 66: 184–199). Importantly, the diverse and complex nature of random peptide libraries have the capacity to provide unique peptide sequences for any target receptor molecules, including those that are well-described and those that are previously undetected (Barry et al. (1996) *Nat. Med.* 2: 299–305). Additionally, the design of phage not only can allow recognition of selective targeting sequences, but also allows rapid isolation of the targeted marker for further characterization. Invented less than 20 years ago (Smith (1985) *Science* 228: 1315–1317), phage display technology has produced valuable targeting ligands to a variety of cell types, both in vitro and in vivo (Pasqualini and Ruoslahti (1996) *Nature* 380: 364–366).

Phage display libraries can provide ready sources of small peptides for targeting cell-specific markers. Phage display libraries are heterogenous mixtures of phage clones, each carrying a different foreign or synthetic DNA insert and, therefore, displaying the corresponding individual synthetic peptide on its surface (Smith & Scott (1993) *Methods Enzymol.* 217: 228–257; Smith & Petrenko (1997) *Chem. Rev.* 97: 391–410). Bacteriophage libraries can be constructed which display random peptides expressed as fusion proteins with a phage protein. See, Barry et al.(1996) *Nature Medicine* 2:299–305; Devlin et al.(1990) 249:404–406; Cwirla et al.(1990) *Proc. Natl. Acad. Sci. USA* 87:6378–6382; and the references cited therein, herein incorporated by reference. Methods for preparing libraries containing diverse populations are also disclosed in Gordon et al.(1994) *J. Med. Chem.* 37:1385–1401; Ecker and Crooke (1995) *BioTechnology* 13:351–360; Goodman and Ro, Peptidomimetics For Drug Design, in "Burger's Medicinal Chemistry and Drug Discovery", Vol. 1, M. E. Wolff (Ed.) John Wiley & Sons 1995, pages 803–861; Blondelle et al.(1995) *Trends Anal. Chem.* 14:83–92; and Sambrook et al., Molecular Cloning: A Laboratory Manual, Cold Spring Harbor Press, 1989. Each of these references are herein incorporated by reference.

Because such libraries allow functional access to the peptide and provide a physical link between the phenotype (displayed peptide) and the genotype (encoding DNA), they lend themselves to a screening process. Clones having desirable binding properties may be separated from non-binding clones by affinity selection. Literally billions of different structures displayed by random phage libraries can be surveyed rapidly for rare binding clones.

Different types of phage display libraries exist, varying for example by the size of the synthetic nucleotide insert, gene location of insert, structure of the displayed synthetic peptide, and number of copies of the synthetic peptide expressed on the surface of the phage (Smith & Petrenko (1997) *Chem. Rev.* 97: 391–410). In phage "landscape libraries," the synthetic peptides are inserted into the phage major coat protein pVIII (see, e.g., copending application Ser. No. 10/289,725, filed Nov. 7, 2002, and references cited therein, herein incorporated by reference). Each phage virion displays thousands of copies of the synthetic peptide in a repeating pattern, subtending a major fraction of the viral surface. The phage body serves as an interacting scaffold to constrain the synthetic peptide into a particular tertiary conformation, creating a defined "landscape" surface structure that varies from one phage clone to the next. Different phage libraries serve different purposes. For example, because of the large number of synthetic peptide copies displayed on "landscape" phage, these particles can be used effectively to create affinity matrices for isolation and purification of peptide-binding proteins.

Synthetic peptides of the invention can be identified and isolated from phage libraries which have been used to select random peptides that bind to target glioma cells. The phage are incubated with the cells of interest to select phage that bind to or are internalized by those cells. After repeated selection of phage bound to specific cells, phage exhibiting affinity or a higher affinity for the cells of interest are further characterized by sequencing of the foreign or synthetic DNA insert (see, e.g., Experimental Example 1). Phage which have undesirable properties such as binding to the plastic used in tissue culture or, e.g., binding to particular populations of normal cells may be removed by use of a depletion or negative subtraction step.

In order to target compounds to particular cells, it is desirable to identify peptides which bind to cell surface markers on that particular cell. It is understood in the art that cell surface molecular expression patterns may include receptors which are common to multiple cell lineages, restricted to one or a few cell lineages, and those which are unique to individual cell types. Additionally, among various types of cells, common receptors may be expressed similarly or at different densities. To identify synthetic peptides that bind to common as well as unique glioma cell markers, three Selection Schemes were used (diagrammed in FIG. 1). To exclude phage that bind to plastic, all three protocols started with incubation of the library in an empty (cell-free) flask made of the same plastic as those used to grow cells. Selection Scheme 1 was designed to identify phage clones which bound to high density RG2 glioma cell surface receptors but might or might not recognize receptors on other cell types, since this scheme did not include depletion or negative selection using other cells. Selection Scheme 2 was designed to identify phage clones showing specific binding to brain cells, so steps of depletion or negative selection using fibroblasts, myoblasts, and hepatocytes were included to remove phage clones that bind to these major cell types. Selection Scheme 3 was designed to identify phage clones showing specific binding to tumor cells of glial origin. In this procedure, the number of copies of each phage clone in the library was significantly reduced in order to enhance the removal of excess phage capable of binding to normal cells. Additionally, the depletion or negative selection steps included astrocytes, and blocking phage were added to the library during the affinity selection steps to minimize non-specific binding of phage.

Confirmation and further characterization of the binding properties of the synthetic peptides was performed using comparative phage "output-input" assays (see, e.g., Experimental Example 1). However, in order to accurately evaluate the affinity of the peptides for their receptors, acoustic wave sensor technology (AWST) may also be used to evaluate the interaction of the synthetic peptide with glioma tissue or brain cell preparations, including preparations enriched for specific cell types. Such techniques are known in the art and are also discussed in copending application Ser. No. 10/289, 725, filed Nov. 7, 2002, and references cited therein, herein incorporated by reference.

Acoustic wave sensor technology (AWST) can be used with tissues and cells from any species, including humans, to confirm the specificity of synthetic peptides selected for binding to rat model glioma cells versus cells of other gliomas. AWST can also be used to evaluate newly-created variant peptides for their binding affinity to other target or non-target cells.

Once synthetic peptides have been selected for binding affinity to glioma cells, they may be modified by methods known in the art. Such modified peptides and the nucleotide sequences encoding them are referred to herein as "variants," and are also provided by the present invention. Methods for creating variants include random mutagenesis as well as synthesis of nucleic acids having nucleotide sequences encoding selected amino acid substitutions, deletions, and/or additions. Variant peptides of various lengths and amino acid composition can be constructed and tested for the effect on binding affinity and specificity. In this manner, the binding properties of the peptide and conferred by the peptide on conjugated compounds may be enhanced.

Thus, variant peptides may be created which exhibit specific binding to and/or internalization by glioma cells of interest. Thus, by "variant" or "variant peptide" is intended a peptide that differs by one or more amino acids from a peptide or motif described herein. Variant peptides may be any length and may include multiple copies of motifs or peptide sequences of the invention. "Variants" also encompass peptides having one or more deletions or additions of amino acid residues when compared to a peptide sequence or motif described herein. Thus, a variant may comprise 1, 2, 3, 4, 5, 6, 7, 8, 9, 10, 11, 12, 13, 14, 15, 16, 17, 18, 19, or 20 or more amino acid substitutions, deletions, and/or additions compared to a peptide or motif described herein.

The synthetic peptides of the invention find further use in targeting genes, proteins, pharmaceuticals, and other compounds to glioma cells. In this manner, the peptides can be used with any vector system for delivery of specific nucleic acids or other compositions to the target cells. Here, the term "nucleic acid" is intended to encompass gene sequences, DNA, RNA, and oligonucleotides as well as antisense nucleic acids. Such targeting may be in vitro, in situ, or in vivo. The synthetic peptides find use in in vitro and/or in situ applications such as, for example, diagnosis of gliomas. The synthetic peptides can be labeled or conjugated with radioisotopes or radionuclides, fluorescent molecules, biotin, enzymes, or any other suitable compound used for localization and/or visualization of particular cell populations. Another in vitro application for which the peptides of the invention find use is affinity purification of cell surface markers which may be specific to tumors, gliomas, or to other cell types. In such applications, the synthetic peptides are linked to an appropriate matrix and used to bind the cell surface marker in solution. In this manner, the synthetic peptides are useful in accurate detection of malignant cells within the brain and to predict response to various anti-cancer treatments.

In vivo applications using the synthetic peptides of the invention include gene therapy. In this regard, it is useful that the invention further provides nucleotide sequences encoding the peptides and variants of the invention, as well as vectors comprising these sequences. Thus, where necessary, the nucleotide sequences can be used in the construction of fusion proteins or vectors for use in diagnostic and/or therapeutic applications. Such methods are known in the art, as are methods for the construction of expression cassettes and the selection of suitable promoters, terminators, enhancers, etc., for desired expression. In order to assess in vivo peptides capable of binding human tumor cells, non-human primates can also be used as a target animal to evaluate binding in a primate species.

A number of vector systems are known for the introduction of foreign or native genes into mammalian cells. These include SV40 virus (see, e.g., Okayama et al.(1985) *Mol. Cell Biol.* 5: 1136–1142); Bovine papilloma virus (see, e.g., DiMaio et al.(1982) *Proc. Natl. Acad. Sci. USA* 79: 4030–4034); adenovirus (see, e.g., Morin et al.(1987) *Proc. Natl. Acad. Sci. USA* 84: 4626; Yifan et al.(1995) *Proc. Natl. Acad. Sci. USA* 92: 1401–1405; Yang et al.(1996) *Gene Ther.* 3: 137–144; Tripathy et al (1996) *Nat. Med.* 2: 545–550; Quantin et al.(1992) *Proc. Natl. Acad. Sci. USA* 89: 2581–2584; Rosenfeld et al.(1991) *Science* 252: 431–434; Wagner (1992) *Proc. Natl. Acad. Sci. USA* 89: 6099–6103; Curiel et al.(1992) *Human Gene Therapy* 3: 147–154; Curiel (1991) *Proc. Natl. Acad. Sci. USA* 88: 8850–8854; LeGal LaSalle et al.(1993) *Science* 259: 590–599); Kass-Eisler et al.(1993) *Proc. Natl. Acad. Sci. USA* 90: 11498–11502); adeno-associated virus (see, e.g., Muzyczka et al.(1994) *J.*

*Clin. Invest.* 94: 1351; Xiao et al.(1996) *J. Virol.* 70:8098–8108); herpes simplex virus (see, e.g., Geller et al.(1988) *Science* 241: 1667; Huard et al.(1995) *Gene Therapy* 2: 385–392; U.S. Pat. No. 5,501,979); retrovirus-based vectors (see, for example, Curran et al.(1982) *J. Virol.* 44: 674–682; Gazit et al. (1986) *J. Virol.* 60: 19–28; Miller, A. D. (1992) *Curr. Top. Microbiol. Immunol.* 158: 1–24; Cavanaugh et al.(1994) *Proc. Natl. Acad. Sci. USA* 91: 7071–7075; Smith et al.(1990) *Mol. Cell. Biol.* 10: 3268–3271); herein incorporated by reference.

Standard techniques for the construction of the vectors of the present invention are well-known to those of ordinary skill in the art and can be found in such references as Sambrook et al. (1989) *Molecular Cloning: A Laboratory Manual,* 2nd ed. (Cold Spring Harbor, N.Y.). A variety of strategies are available for ligating fragments of DNA, the choice of which depends on the nature of the termini of the DNA fragments; appropriate choices can be readily made by those of skill in the art.

The peptides of the invention can be used with any mammalian expression vector to target the expression system to the appropriate target glioma cells. In this aspect, methods such as those described by Wu et al.(1991) *J. Biol. Chem.* 266: 14338–14342; Wu and Wu (1988) *J. Biol Chem.* 263: 14621–14624; Wu et al. (1989) *J. Biol. Chem.* 264: 16985–16987; Zenke et al.(1990) *Proc. Natl. Acad. Sci. USA* 87: 3655–3659; Wagner et al. *Proc. Natl. Acad. Sci.(*1990) 87: 3410–3414; can be used.

Where the peptides of the invention are targeting a gene for expression in the target glioma cells, the gene to be expressed will be provided in an expression cassette with the appropriate regulatory elements necessary for expression of the gene. Such regulatory elements are well known in the art and include promoters, terminators, enhancers, etc.

The peptides of the invention may also be utilized to target compounds and compositions such as liposomes, polylysine or other polycation conjugates, and synthetic molecules for delivery to the target cells. See, for example, de Haan et al.(1996) *Immunology* 89: 488–493; Gorlach et al.(1996) *DTWDTsch Tierarytl Wochenschr* 103: 312–315; Benameur et al.(1995) *J. Phar. Pharmacol.* 47: 812–817; Bonanomi et al.(1987) *J. Microencapsul* 4: 189–200; Zekorn et al.(1995) *Transplant Proc.* 27: 3362–3363. Thus, the peptides of the invention can be used as free peptides or they can be conjugated or linked to other compounds such as cytotoxic agents including radioisotopes, pharmaceutical compounds, gene therapy viral or non-viral vectors, or to other compounds performing cytotoxic or delivery functions.

In this manner, the peptides of the invention can be used to provide therapies for gliomas as well as other tumor cells or abnormal cells to which the peptides of the invention may bind. That is, for example, genes, proteins, or pharmaceuticals can be directed to target cells in those patients suffering from the particular tumor or disease.

More particular embodiments of approaches in which the peptides of the invention can be used to direct substances to tumor cells for therapeutic purposes include but are not limited to delivery of suicide genes, prodrug activating genes, tumor suppressor genes, cytokines mediating anti-tumor responses and antisense DNA to block action of growth factors for the treatment of cancers of the CNS including brain tumors (see, e.g., Chung et al.(1998) *Surg. Oncol. Clin. N. Am.* 7: 589–602; Maria et al.(1997) *J. Child Neurol* 12: 77–84). In the same manner, the peptides of the invention may be utilized to target pharmaceuticals such as, for example, chemotherapeutic agents to treat cancers of the CNS including gliomas. Where desirable, the peptides of the invention may be conjugated or linked to more than one other compound. Examples of chemotherapeutic agents include methotrexate, adriamycin, cyclophosphamide, and the like. The peptides of the invention can also be used to deliver other compounds such as antiviral agents and nucleotide analogues to the CNS. Further examples of substances which can be targeted to the CNS by the peptides of the invention include the neuropharmaceutical agents listed in U.S. Pat. No. 5,527,527 (column 3, lines 21–65), herein incorporated by reference.

Thus, classes of neuropharmaceutical agents which can be used in this invention include proteins, antibiotics, adrenergic agents, anticonvulsants, small molecules, nucleotide analogs, chemotherapeutic agents, anti-trauma agents, peptides and other classes of agents used to treat or prevent a neurological disorder. Examples of proteins include CD4 and superoxide dismutase (including soluble portions thereof), growth factors (e.g., nerve growth factor (NGF), brain-derived neurotrophic factor (BDNF), ciliary neurotrophic factor (CNTF), neurotrophins 3, 4, and 5 (NT-3, 4, and 5) or fibroblast growth factor (FGF)), lymphokines or cytokines (e.g., interferon or interleukins (IL-2)) or antagonists thereof, neurotrophic factors, dopamine decarboxylase and tricosanthin. A neurotrophic factor is defined as a factor capable of maintaining neuron survival or neuron regeneration or differentiation; the properties of these neurotrophic factors are known in the art. Examples of antibiotics include amphotericin B, gentamycin sulfate, and pyrimethamine. Examples of adrenergic agents (including blockers) include dopamine and atenolol. Examples of chemotherapeutic agents include adriamycin, methotrexate, cyclophosphamide, etoposide, and carboplatin. An example of an anticonvulsant which can be used is valproate and an anti-trauma agent which can be used is superoxide dismutase. Examples of peptides would be somatostatin analogues and endephalinase inhibitors. Nucleotide analogs which can be used include azidothymidine (hereinafter AZT), dideoxyinosine (ddI) and dideoxycytodine (ddC).

The synthetic peptides of the invention may be provided as pharmaceutical compositions suitable for parenteral (e.g., subcutaneous, intradermal, intramuscular, intravenous and intraarticular), oral or inhalation administration. Alternatively, pharmaceutical compositions of the present invention may be suitable for administration to the mucous membranes of the subject (e.g., intranasal administration). It is recognized that intranasal administration could be used to target substances to olfactory neurons, which are otherwise difficult to access. In the same manner, intraocular administration could be used to target substances to the optic nerve.

Pharmaceutical compositions comprise at least one synthetic peptide of the invention and at least one other compound, which may or may not be conjugated to the synthetic peptide. Typically, the other compound is intended to help treat a disease or symptom of a disease; for example, the other compound may be a chemotherapeutic agent intended to shrink a target tumor in a cancer patient. While in some applications the other compound will be conjugated to the synthetic peptide of the invention, in other applications improved results may be obtained where the other compound and the synthetic peptide are not conjugated to each other.

Where needed, the pharmaceutical compositions of the present invention may be administered by direct delivery to the central nervous system by intrathecal injection into cerebrospinal fluid or directly into the brain, for example, into the vicinity of the cancer cells to be treated. The formulations may be conveniently prepared in unit dosage form and may be prepared by any of the methods well-known in the art. Any inert pharmaceutically-acceptable carrier may be used, such as saline, or phosphate-buffered saline, or any such carrier in which the compositions of the present invention have suitable solubility properties for use in the methods of the present invention. Reference is made to Osol, ed. (1980) *Remington's Pharmaceutical Sciences* (Merck Publishing Company, Easton, Pa.) for methods of formulating pharmaceutical compositions. The peptides of the invention could be used in conjunction with any other known methods for delivering substances to the brain, including but not limited to those described in U.S. Pat. Nos. 4,866,042; 5,527,527; 5,124,146; 5,672,683; and 5,716,614.

The following experiments are offered by way of illustration and not by way of limitation.

EXPERIMENTAL

Model gliomas have been developed for understanding tumor biology and developing and testing diagnostic and therapeutic techniques for gliomas. The model glioma cell line RG2 (CRL-2433, available from American Type Culture Collection (ATCC), 10801 University Boulevard, Manassas, Va. 20110-2209) is an undifferentiated malignant glioma from the brain of a Fischer rat pup following injection of N-ethyl-N-nitrosurea into the pregnant dam (Ko et al. (1980) *Acta Neuropathol. (Berl.)* 51: 23–31). Inoculation of this cell line into Fischer 344 rats generates a well-established, easily reproducible animal model of malignant glioma having biological characteristics closely resembling human glioblastoma, including infiltrative growth pattern, non-immumogenicity in syngeneic hosts, and poor response to therapy (see, e.g., Aas et al. (1995) *J. Neurooncol.* 23: 175–183; Ceberg et al. (1995) *J. Neurosurg.* 83: 86–92). RG2 cells have been utilized extensively for understanding tumor biology and for developing and testing diagnostic and therapeutic techniques for gliomas (reviewed by Barth (1998) *J. Neurooncol.* 36: 91–102).

In the following experiments, a single phage display library was used in varying selection schemes. This f8-1/8-mer landscape phage display library was constructed by inserting eight random amino acids at the N-terminus of the major phage coat protein pVIII (Petrenko et al. (1996) *Protein Eng.* 9: 797–801). Each virion in this library displays thousands of copies of the peptide in a repeating pattern subtending a major fraction of the viral surface. The phage body serves as an interacting scaffold to constrain the peptide into a particular tertiary conformation, creating a defined "landscape" surface structure that varies from one phage clone to the next. Because of the large number of peptide copies on landscape phage, these particles can be used effectively not only to identify cell-specific ligands, but also to create affinity matrices for isolation of peptide-binding proteins (see, e.g., Smith et al. (1998) *J. Immunol. Methods* 215: 151–161; copending application Ser. No. 10/289,725, filed Nov. 7, 2002, herein incorporated by reference in their entirety). The size of the library was approximately $2 \times 10^9$ phage.

All general methods of handling phage display libraries, including phage propagation, purification, titering, production of pure phage clones, and isolation of phage DNA are described in detail in *Phage Display: A Laboratory Manual* (Cold Spring Harbor Laboratory Press, Cold Spring Harbor, N.Y. (2001)).

EXAMPLE 1

Selection Schemes for Affinity Selection of Phage

Selection of phage clones which bind to glioma cell-specific receptors was performed as described by Barry et al. (1996) *Nat. Med.* 2: 299–305, with the modifications described below. Generally, the selection of phage began with depletion or negative selection of clones that bound readily to plastic by incubating a library aliquot in 25 cm² plastic flasks. Selection Schemes 2 and 3 incorporated additional depletion or negative selection steps. In Selection Schemes 1 and 2, a library aliquot containing an estimated 100 copies of each phage clone was used, while in Selection Scheme 3, a library aliquot containing an estimated 10 copies of each phage clone was used.

Defined Selection Schemes were developed to identify peptides that bound to or preferentially bound to glioma cells. Both the RG2 (CRL-2433) and F98 (CRL-2397) rat glioma cell lines (available from the American Type Culture Collection (ATCC), 10801 University Boulevard, Manassas, Va. 20110-2209) are undifferentiated malignant gliomas from the brains of Fischer rat pups following injection of N-ethyl-N-nitrosurea into the pregnant dam (Ko et al. (1980) *Acta Neuropathol (Berl)* 51: 23–31). Normal rat cells included the following cell lines, all obtained from the ATCC: 27FR fetal skin fibroblasts (ATCC # CRL-1213), H9c2(2-1) cardiac myoblasts (ATCC # CRL-1446), CTX TNA2 astrocytes (ATCC # CRL-2006), and BRL 3A hepatocytes (ATCC # CRL-1442). All cells were grown in media as recommended by ATCC and incubated at 37° C., 5% $CO_2$. RG2 and F98 glioma cells and cardiac myoblasts H9c2(2-1) were cultured in DMEM adjusted to contain 1.5 g/L sodium bicarbonate, 4.5 g/L glucose, and 10% fetal bovine serum (FBS). Astrocytes and fibroblasts were grown in DMEM containing 4.5 g/L glucose and 10% FBS. Hepatocytes were grown in minimum essential medium Eagle with 2 mM L-glutamine, 0.1 mM non-essential amino acids, 1 mM sodium pyruvate, and 10% FBS.

For use in screening protocols, all cell types were grown in 25 cm² polystyrene flasks for 48 hours to sub-confluent monolayers. To accomplish this, RG2 cells were initially plated at $2.5 \times 10^6$ cells/flask, myoblasts, hepatocytes and fibroblasts were plated at $1 \times 10^6$ cells/flask, and astrocytes and F98 glioma cells were plated at $2 \times 10^6$ cells/flask.

Phage Selection.

The method of Barry et al. ((1996) *Nat. Med.* 2: 299–305) with our modifications was used for selection protocols. Three selection schemes were used (see FIG. 1). Selection began with depletion of phage clones binding to plastic. Briefly, an aliquot of the primary library in 2 ml of washing/blocking buffer (0.1% BSA, 0.1% Tween 20 in DMEM) was added to an empty 25 cm² tissue culture flask ("depletion flask") and incubated for 1 hour at room temperature. At the same time, cells were incubated for 1 hour at 37° C., 5% $CO_2$ in serum-free medium that was removed immediately prior to application of the phage. The washing/blocking buffer, now containing phage that did not bind to the plastic, was transferred from the depletion flask to the flasks containing cells and incubated for 1 hour at room temperature.

Following incubation with the RG2 cells, unbound phage were washed away with washing/blocking buffer. In Selection Scheme 1, cell-surface bound phage were treated with 1 ml elution buffer (0.1M glycine-HCl, pH 2.2) for 10 minutes on ice ("RG2 glioma flask 1"; see FIG. 1). The eluate was removed from the flask, neutralized with 175 µl of 1 M Tris solution (pH 9.1) and concentrated by centrifugation in a Centricon 100 kD (Fisher Scientific) to an approximate volume of 150 μl. To recover phage clones internalized by the RG2 cells, cells were scraped from "RG2 glioma flask" 2 in 5 ml DMEM and pelleted by centrifugation at 130×g for 10 minutes; the DMEM was then removed and the cell pellet was lysed with 200 μl of lysis buffer (DOCNa buffer: 2% DOCNa, 10 mM Tris, 2 mM EDTA, pH 8.0).

In Selection Schemes 2 and 3, the phage recovery procedure was the same as for Selection Scheme 1 except that both phage fractions (eluted and lysis) were obtained sequentially from the same flask, as diagrammed in FIG. 1. These phage fractions were amplified separately in bacteria and used in subsequent rounds of selection for RG2 tumor cell recognition.

The remaining rounds of affinity selection were accomplished as described above. In each round, the enrichment in the phage population of cell-binding phage was determined via titering of input and output phage for each round. Following the fourth affinity selection round in Selection Schemes 1 and 2 and the sixth affinity-selection round in Selection Scheme 3, phage DNAs were isolated and the foreign or synthetic nucleotide sequence was determined. These sequences were then translated to determine the peptide sequences responsible for tumor cell binding.

Quantitation of Binding Specificity.

In order to evaluate the binding specificity conferred by the peptides, various phage clones were incubated with RG2 glioma cells. Two control phage were compared to the RG2 affinity-selected candidate phage clones (see FIG. 3). The two control phage were the phage library vector f8-5 (which does not express any foreign peptides) and phage clone 1F20 (which expresses a random peptide). For the quantitation assay, RG2 cells were grown in 25 $cm^2$ flasks for approximately 48 hours to sub-confluence. One hour prior to application of phage, the normal media was replaced with serum-free media and incubation was continued. Each phage clone ($10^9$ cfu/flask) was added to a flask of cells in 2 ml of washing/blocking buffer and incubated for 1 hour at room temperature. Following incubation, unbound phage were removed by washing the cells remaining in the flasks 8 times with 4 ml of cold washing/blocking buffer for 5 minutes per wash. Cell surface-bound phage were recovered by incubation with 1 ml of elution buffer for 10 minutes on ice. The eluate was removed from flasks and neutralized with 1 M Tris. Cells were washed again two times with washing/blocking buffer and lysed by incubation with 1 ml lysis buffer for 30 min at room temperature; the lysate was processed as above. Phage titers were determined by infection of bacteria and are presented in FIG. 3 as a ratio of output to input phage. All analyses were performed in triplicate.

Evaluation of Binding Selectivity.

To evaluate the selectivity of the binding conferred by the identified peptides, RG2 affinity-selected phage clones were incubated with RG2 glioma cells and various control cell lines, including F98 glioma, CTX TNA2 astrocytes, 27FR fibroblasts, H9c2(2-1) cardiac myoblasts, and BRL 3A hepatocytes. Comparison of phage titers was accomplished as for binding specificity above.

Comparison of Results.

The three Selection Schemes used herein (diagrammed in FIG. 1) were developed to identify peptides that would bind specifically to glioma cell surface markers that are commonly found on other cell types as well as to unique glioma cell surface markers. In order to exclude phage that bind to plastic, all three Selection Schemes began with a depletion step in which the library aliquot was incubated in an otherwise empty flask made of the same plastic as those used for cell culture.

Selection Scheme 1 was designed to identify synthetic peptides which bind to high density RG2 glioma cell surface markers. Because Selection Scheme 1 did not include a depletion step using other cells, phage clones identified with this selection scheme might or might not bind to other cell types. Selection Scheme 2 included depletion or negative selection steps using three different cell types—fibroblasts, myoblasts, and hepatocytes—which represent major cell types in the body. These additional negative selection steps were included in order to remove phage clones that bind these cell types and identify phage clones having binding specificity to brain tissue.

In Selection Scheme 3, a smaller phage library aliquot was used in order to better remove undesirable phage clones and to better identify and isolate phage clones that might be selective for tumor cells of glial origin. The phage library aliquot used included only an estimated 10 copies of each phage clone rather than the estimated 100 copies of each phage clone used in Selection Schemes 1 and 2. Also, the array of normal cells in the negative selection steps was changed to include astrocytes rather than fibroblasts, and blocking phage were added to the library incubation medium to minimize non-specific binding.

Results from Selection Scheme 1.

As shown in FIG. 2 (upper graph), the ratio of output to input phage for cell-surface-bound phage increased from one round to the next, indicating successful selection for phage clones that bind to RG2 glioma cells. As shown in FIG. 2 (lower graph), after the fourth round, the ratio of output to input phage isolated after cell lysis was approximately 320-fold higher than for the original library. This increase demonstrated effective selection for phage clones that bind to and are internalized by RG2 glioma cells.

Peptide Sequences Identified Using Selection Scheme 1.

After the fourth round in both experiments, phage DNAs were isolated and the foreign or synthetic nucleotide sequence in each phage clone was determined. Translation of these sequences revealed the amino acid sequences of the peptides conferring binding specificity on the phage (shown in Table 1).

TABLE 1

Peptide Sequences from Selection Scheme 1

| Sequence | Frequency* | SEQ ID NO: |
|---|---|---|
| Elution Buffer Fraction | | |
| VDLPEHGK | 9 | 1 |
| VGLPEHTQ | 5 | 9 |
| VGLPEHSA | 4 | 3 |
| VDLPTHSS | 7 | 4 |
| VDLPEHRQ | 1 | 5 |
| VDLPTHQS | 1 | 6 |
| VDLPTHNQ | 1 | 7 |
| VDLPQHGQ | 1 | 10 |
| DTTKNGSG | 1 | 11 |
| random | 1 | — |
| Lysis Buffer Fraction | | |
| ELRGDSLP | 10 | 12 |
| EVRGDSLP | 2 | 13 |
| VDLPSHPE | 1 | 14 |
| VNLPEHPE | 2 | 15 |
| VDLPRSDT | 1 | 16 |
| HTTKEQMA | 1 | 17 |
| random | 12 | — |

*frequency = number of phage clones shown to be displaying a peptide having this sequence.

From the above information for cell surface-binding phage (Elution Buffer Fraction), a motif of six amino acids, $V_{(D/G)}LP_{(E/T)}H$ (SEQ ID NO:8) was identified. For phage recovered from whole cell lysate, (Lysis Buffer Fraction) several different types of peptide sequences were found. Three of the sequences were similar to those from the cell-surface fraction.

Additionally, peptide sequences were recovered which contained the "RGD" sequence motif, which is known to bind to integrins (see, e.g., Ruoslahti (1997) Kidney Int. 51:1413–1417; Akiyama (1996) Hum. Cell 9: 181–186). Two kinds of RGD sequences were obtained, differing from each other by the amino acid in the second position: the first group contains leucine (L) in the second amino acid position, while the second group contains valine (V) in that position. These amino acids have non-polar side chains that differ only in length and thus are likely to perform the same role in binding. Recovering two similar, but not identical, sequences is indirect proof of the specificity of the selection process.

Binding Specificity and Selectivity of Identified Phage Clones.

Phage clones displaying the peptide sequences shown in Table 1 were tested further in a binding assay to evaluate binding affinity and to confirm binding specificity to glioma cells. As shown in FIG. 3, two cell-surface binding clones (#3 and #19) demonstrated the highest ratio of output to input phage and thus had the highest apparent binding affinity. In comparison, two control phage clones showed negligible binding to glioma cells. One control phage clone was the phage library vector f8-5, which does not express any foreign peptides, and the second control was a phage clone 1F20 that expresses a random peptide. Binding of both controls to glioma cells was negligible and approximately one thousand fold lower than that of RG2 affinity-selected clones.

Additionally, the phage clone showing the highest binding affinity to RG2 cells was assayed for its binding selectivity of ability to bind to various cell types. This phage clone displayed the synthetic peptide sequence VGLPEHTQ (SEQ ID NO:19); results are shown in FIG. 4. Binding of this phage clone to another glioma cell line, F98, was 41% of its RG2-binding level. Binding of this phage clone to normal astrocytes was 64% of its RG2-binding level. Binding of this phage clone to unrelated normal control cells (hepatocytes, myoblasts, and fibroblasts) was approximately 5 fold lower than the RG2-binding level. Thus, overall the binding selectivity of this phage clone was in the range of 2 to 5 fold, depending on the type of control cells used for comparison.

Similar selectivity studies were performed for the phage clone displaying the synthetic peptide ELRGDSLP, which was recovered from the lysis buffer fraction (results shown in FIG. 5). While this phage clone bound to glioma cells, it also bound to cells which are non-brain in origin, such as hepatocytes, myoblasts and fibroblasts. This binding to normal cells may be due to the presence of other RGD-binding receptors on those cells. However, this phage clone showed approximately 63-fold higher binding to glioma cells compared to its binding to normal brain cells (astrocytes).

Selection Scheme 2.

The values of phage output/input ratios for four rounds of RG2 affinity selection are shown in FIG. 6 (upper graph: "elution buffer" fraction; lower graph: "lysis buffer" fraction). As in Selection Scheme 1, the enrichment procedure was stopped when a significant increase in phage associated with the cells was observed, i.e., after the fourth round.

Peptide Sequences Identified Using Selection Scheme 2.

Among phage clones isolated from the elution fraction, a family of peptides was identified (see Table 2) that shared the $V_{(D/G)}LP_{(E/T)}H$ motif also identified in Selection Scheme 1.

TABLE 2

Peptide Sequences from Selection Scheme 2

| Sequence | Frequency | SEQ ID NO: |
|---|---|---|
| Elution Buffer Fraction | | |
| VDLPQHGG | 4 | 18 |
| VDLPTHTS | 1 | 19 |
| VNLPEHAQ | 2 | 20 |
| VGLPEHQP | 1 | 21 |
| DTTKTSAG | 1 | 22 |
| DSTKIGTS | 1 | 23 |
| DSTKASDA | 1 | 24 |
| DTTQSMHT | 1 | 25 |
| DSTKSTNS | 1 | 26 |
| DSTKAVAL | 1 | 27 |
| DSTKSGNM | 1 | 28 |
| DTTKGPGT | 1 | 29 |
| DGTKMAGG | 1 | 30 |
| random | 4 | — |
| Lysis Buffer Fraction | | |
| DTTKGGNP | 1 | 31 |
| DDTKHSLP | 1 | 32 |
| DTTRTHMP | 1 | 33 |
| DSTRGSPA | 1 | 34 |
| DTTRLSDQ | 1 | 35 |
| DNTRVAAP | 1 | 36 |
| DDTRYSSA | 1 | 37 |
| DETLYGIS | 1 | 38 |
| DYDMTKNT | 1 | 39 |
| random | 22 | — |

While nearly all of the peptides identified from the elution buffer fraction of Selection Scheme 1 contained the $V_{(D/G)}LP_{(E/T)}H$ motif (see Table 1), only about a third of all the sequences identified from the elution buffer fraction of Selection Scheme 2 contained this motif (see Table 2). In addition, a new family of peptides was isolated that shared the motif $D_{(T/S)}TK$ (SEQ ID NO:40). In the "lysis buffer" fraction, some of the identified peptides shared a similar motif of three amino acids: $D_{(T/S)}K$ (SEQ ID NO:41). The sequences in this family were highly diverse, being isolated only once among the phage clones tested and each having different flanking amino acids.

Binding Selectivity of Phage Clones.

One phage clone from the elution buffer fraction and one from the lysis buffer fraction were tested for selectivity of binding to rat glioma cells. Binding selectivity was evaluated by quantitation of cell-associated phage after incubation of the phage with glioma cells. The phage clones displaying the DSTKSGNM peptide was isolated from the elution buffer fraction. As shown in FIG. 7, this phage clone showed highly selective binding to RG2 glioma cells when compared to normal astrocytes (25 fold increase) or to other normal cells, including fibroblasts, myoblasts, and hepatocytes (32 to 86 fold increase). This clone demonstrated even better binding to cells of another rat glioma, F98, than to RG2 glioma cells.

The second phage clone tested in these experiments displayed the synthetic peptide DYDMTKNT and was isolated from the lysis buffer fraction. This phage clone contained the DMTK motif (SEQ ID NO:42) in the middle of the synthetic peptide sequence and also showed very selective binding for both types of glioma cells tested (FIG. 8).

Selection Scheme 3.

Additional modifications were made to the selection conditions in Selection Scheme 3. First, the additional negative selection or depletion steps included in Selection Scheme 2 did not exclude phage bearing peptides containing the motif sequence $V_{(D/G)}LP_{(E/T)}H$, which was found to bind to all cell types tested. This indicated that the depletion of phage clones that bound to normal cells was not complete. To address this problem, the initial library aliquot used in Selection Scheme 3 contained 10-fold fewer phage than had been used in the first two Selection Schemes. Another problem with Selection Scheme 2 was the isolation of many random peptide sequences, which demonstrated that non-specific binding of the library phage to RG2 cells had occurred. In order to better block nonspecific interactions, "blocking phage" were added to the regular blocking buffer with BSA. These blocking phage were nonspecific to the target cells, but could compete for binding sites with other nonspecific phage clones in the library. Finally, to further enhance the selection of brain tumor-specific phage, astrocytes were used in a negative selection or depletion step.

Recovery of Cell-Associated Phage from RG2 Glioma Cells.

In the first round of Selection Scheme 3, phage were collected in two sequential steps from the same flask with RG2 cells. In each following round, selection was performed using two separate flasks, one for the "elution buffer" fraction and the other for the "lysis buffer" fraction. The corresponding phage fractions were saved, amplified, and used for the next round of selection. Phage DNAs were isolated and sequenced when maximum enrichment in cell-associated phage were observed. As shown in FIG. 9 (upper graph), maximum enrichment occurred after the sixth round for phage eluted from the cells ("elution buffer" fraction), while maximum enrichment occurred after the fifth round for phage isolated from the "lysis buffer" fraction (lower graph).

Peptide sequences identified using Selection Scheme 3. Twenty-one phage clones were randomly isolated from the above selection scheme, and their DNAs were isolated and sequenced. The foreign or synthetic nucleotide sequences encoding the synthetic peptides were translated (results shown in Table 3).

TABLE 3

Peptide Sequences from Selection Scheme 3

| Sequence | Frequency | SEQ ID NO |
|---|---|---|
| Elution Buffer Fraction | | |
| DLTKSTAP | 9 | 43 |
| DTTKSTTT | 1 | 44 |
| EPVQPHST | 1 | 45 |
| Lysis Buffer Fraction | | |
| ESRGDSYA | 2 | 46 |
| DLTKSSAP | 1 | 47 |
| DTTKLTNQ | 1 | 48 |
| DNAIYTYQ | 2 | 49 |
| ASNHVMYQ | 4 | 50 |

In phage recovered in the "elution buffer" fraction, the diversity of phage clones was much lower than for those isolated from Selection Schemes 1 and 2; nine out of eleven of the synthetic peptides were identical. However, some peptides contained a $D_{(T/L)}TK$ motif (SEQ ID NO:51), which differed from similar peptides isolated from Selection Schemes 1 and 2 by the presence of L (leucine) in the second position. Phage collected from the "lysis buffer" fraction were more diverse. This fraction included phage displaying synthetic peptides containing the $D_{(T/L)}TK$ motif and a group of identical peptide sequences ASNHVMYQ (SEQ ID NO:50). This fraction also contained two phage expressing peptides that contained the well-known RGD motif (see, e.g., Ruoslahti (1997) *Kidney Int.* 51: 1413–1417; Akiyama (1996) *Hum. Cell* 9: 181–186).

Binding Selectivity of Phage Clones.

One phage bearing the synthetic peptide DLTKSTAP showed high binding selectivity for RG2 cells when compared to its binding to hepatocytes, myoblasts, and fibroblasts (see FIG. 10). The binding selectivity of this phage clone, which was in the range of 185-fold to 615-fold, was higher than that of any previously tested phage clone. Selectivity of binding of this phage clone to RG2 glioma cells was approximately 14-fold higher than binding to astrocytes (see FIG. 10).

The second phage clone tested, which displayed the synthetic peptide ESRGDSYA, was similar to a phage clone identified in Selection Scheme 1 which displayed the synthetic peptide ELRGDSLP. Both synthetic peptides had five identical amino acids at positions 1, 3, 4, 5, and 6, but differed at the remaining three positions. Both phage clones showed similar selectivity binding patterns (compare FIGS. 5 and 11), but the output/input phage ratio was significantly lower for the ELRGDSLP phage clone. This difference may reflect the amount of the initial library aliquot used in Selection Scheme 2 versus Selection Scheme 3.

Comparison of Motifs Identified Using the Selection Schemes.

Three major families of peptides with the following consensus motifs were identified. The motif in the first family, $V_{(D/G)}LP_{(E/T)}H$, consists of six amino acid residues, four of which were identical for all family members (amino acids at positions one, three, four, and six), while variable amino acids were found in two other positions. The second amino acid in this sequence was occupied by either aspartic acid or glycine; these amino acids have an acidic side chain and an uncharged polar side chain, respectively. The fifth amino acid in this sequence was occupied by either glutamic acid (acidic side chain) or threonine (uncharged polar side chain). Both of these amino acids have similar side chains to those of the second amino acid, demonstrating that their presence within the sequence is not random. A database search of the $V_{(D/G)}LP_{(E/T)}H$ motif was performed against protein sequences in the PIR-PSD, PIR-NRL3D, FAM-BASE, iProClass (PIR+Swiss-Prot), and NREF databases for comparison to known proteins. Among a few proteins that contain this motif, none was a commonly recognized ligand for glial cell tumors.

The second family of peptides contained the motif $D_{(T/S/L/M)}TK$ (SEQ ID NO: 52). Different examples of peptides containing this motif were identified in each Selection Scheme. The sequence DTTK (SEQ ID NO:53) was identified once from Selection Scheme 1, while the sequence $D_{(T/S)}TK$ was identified many times in Selection Scheme 2. The sequence DMTK was also identified in Selection Scheme 2, and the sequence $D_{(T/L)}TK$ was identified many times in Selection Scheme 3. These sequences were combined to arrive at the $D_{(T/S/L/M)}TK$ motif. In this motif, the second amino acid has nonpolar (leucine) or uncharged polar side chains of different lengths (threonine or serine) which very likely perform the same function within the sequence and are therefore interchangeable. The isolation of very similar peptide sequences in three independent experiments from approximately $2 \times 10^9$ variants demonstrates a remarkable specificity of the cell recognition process. While database searches revealed many proteins containing these motifs, only a few of these proteins are thought to be involved in brain cell function.

The third family of peptides includes phage clones displaying peptides with the $E_{(L/S/V)}$RGDS motif (SEQ ID NO: 54). These peptides were identified in the "lysis buffer" fraction of Selection Schemes 1 and 3. All peptide sequences within this family contain the well-known RGD motif, which is known to bind to a number of cell surface receptors. In addition, this family of peptides contains the similar four amino-acid motif RGDS, which is present in fibronectin (PIR-PSD protein database), a well-known ligand for a number of integrins expressed on brain cells (see generally, e.g., Zamir & Geiger (2001) *J. Cell Sci.* 114: 3583–3590). Interestingly, integrins αvβ3 and αvβ5, which bind to vitronectin, are overexpressed on brain tumors (Taga et al. (2002) *Int. J. Cancer* 98: 690–697). Synthetic RGDS peptide has been shown to block integrin-mediated adhesion to vitronectin (Bafetti et al. (1998) *J. Biol. Chem.* 273: 143–149).

Phage clones belonging to this third family and expressing the ELRGDSLP synthetic peptide were used to affinity-isolate the receptor to which the peptide bound.

The ELRGDSLP phage clone was tested further for binding to four different human glioma cell lines: SW1088, M059K, A172, and HS 683, all obtained from the ATCC. While binding differed among these cell lines, the ELRGDSLP peptide conferred pronounced glioma-specific binding properties on phage clones displaying it.

EXAMPLE 2

Identification of Cell Surface Markers to Which Synthetic Peptides Bind

Experiments were performed to isolate and purify the RG2-cell-specific protein that was responsible for binding of the ELRGDSLP phage clone to glioma cells. The basic approach was to perform precipitation of RG2 cell membrane proteins by using the phage clone to form an affinity matrix.

To prepare the RG2 cell membrane proteins, RG2 glioma cells were grown in 25 cm² tissue culture flasks. The growing medium was removed from the flasks and cells were collected in PBS buffer containing protease inhibitors. Cells were then pelleted by centrifugation and lysed with octylglucoside buffer (10 mM Tris-HCl, pH 7.5, 140 mM NaCl, 10 mM octylglucoside (Sigma), and protease inhibitor cocktail (Sigma); 5 ml per flask). The cell lysate was clarified by centrifugation and the supernatant containing cell membrane proteins was then used for isolation of glioma-specific receptor proteins.

Cross-linked phage were prepared by the method of Smith et al. (1998) (*J. Immunol. Methods* 215: 151–161) using a water-soluble, multifunctional dextran polymer. After that, ELRGDSLP cross-linked phage were incubated with the clarified lysate of RG2 cells. Following incubation, the crosslinked phage-receptor protein complexes were pelleted by centrifugation at 10,000 rpm for 15 minutes. Phage particles that were not cross-linked remained in the buffer and were discarded.

Proteins were then eluted from the phage-receptor protein matrix with low pH buffer. Protein eluates were run on an SDS polyacrylamide gel and blotted to PVDF membranes (Immobilon-P transfer membranes, from Millipore). As controls, samples of whole cell lysates were run on the same gel. The gel was then used to prepare a Western blot.

The phage clone used in this experiment displayed the ELRGDSLP peptide and thus contains the RGD motif, which is known to bind integrins. Accordingly, antibodies to several known RGD-binding proteins were used as probes for protein recognition on the Western blot. These antibodies included antibodies to the αv, β3, and β1 integrins and also included antibodies to CD44, the receptor for hyaluronic acid which is known to be expressed on glioma cells. Two kinds of anti-CD44 antibodies were used, one of which recognizes all CD44 isoforms and the other of which recognizes only "standard" CD44, also known as "CD44s" or "CD44H." The anti-integrin antibodies did not produce any positive signal, while reaction with the CD44 antibodies detected one pronounced band having a molecular weight of approximately 97 kD. A Western blot using antibodies which specifically recognize CD44s ("OX-49 antibodies") also produced a positive signal corresponding to a protein having a molecular weight of approximately 97 kD. This Western blot showed that the CD44s protein was present in whole cell lysates of RG2 and F98 glioma cells (moderate staining) as well as in the phage-purified protein sample from RG2 cells (intense staining). A very weak band was observed in protein samples from normal astrocytes, and no staining was seen in the negative control sample of hepatocytes.

Thus, this experiment demonstrated the isolation and identification of the glioma-specific receptor CD44s using a phage clone selected from a phage display library for its ability to selectively bind to RG2 glioma cells.

EXAMPLE 3

Therapy in an Animal Model i. Induction of Model Glioma in Experimental Animals

Fischer 344 rats are injected with RG2 cells so as to induce the formation of malignant gliomas. At various times, brain biopsies are taken from representative rats from the population. Portions of these biopsies are frozen and evaluated histochemically. Tissue samples are homogenized and assayed for the presence or absence of cell surface markers that bind to an array of synthetic peptides.

ii. In Vivo Delivery of Pharmaceuticals

Synthetic peptides are conjugated to methotrexate to form a pharmaceutical composition. Each test rat is sedated, and an intraarterial catheter placed in the internal carotid artery so as to deliver the pharmaceutical composition directly to the rat's brain as a slow injection. If the location of the tumor is known, then intratumoral injections are preferred. During injection, the rats are monitored for signs associated with adverse reactions such as anaphylaxis, and should such reactions occur, administration of the vector is suspended and appropriate treatments initiated.

iii. Studies of Pharmaceutical Efficacy

Brain biopsies are taken from representative test and control animals at one, two, three, four, six and eight weeks following the injection of the pharmaceutical composition and monthly thereafter. Biopsies are compared for progression of tumor development, etc.

EXAMPLE 4

Diagnosis and Prognosis in Human Patients

Gliomas from human patients are assayed for the presence or absence of cell surface markers that bind to synthetic peptides. The presence or absence of particular cell markers and their relative amounts are compared to the eventual outcome of the patient's case and also to other treatment parameters such as whether surgical resection was performed, whether radiotherapy was used, etc. Correlations are sought between aspects of the patient's treatment and outcome and the presence, absence, quantity, etc. of an array of cell surface markers. If a significant correlation is found between one or more parameters and a particular cell surface marker, further analysis is conducted to evaluate whether the cell surface marker and corresponding synthetic peptide are meaningful diagnostic and/or prognostic tools.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

The invention claimed is:

1. A synthetic peptide consisting of the amino acid sequence ELRGDSLP (SEQ ID NO:12), wherein said synthetic peptide exhibits preferential binding to RG2 glioma cells when compared to its binding to astrocytes.

2. A synthetic peptide consisting of the amino acid sequence DSTKSGNM (SEQ ID NO:28), wherein said synthetic peptide exhibits preferential binding to RG2 glioma cells when compared to its binding to astrocytes.

3. A synthetic peptide consisting of the amino acid sequence DYDMTKNT (SEQ ID NO:39), wherein said synthetic peptide exhibits preferential binding to RG2 glioma cells when compared to its binding to astrocytes.

4. A synthetic peptide containing the motif $V_{(D/G)}LP_{(E/T)}H$ (SEQ ID NO:8), wherein said synthetic peptide is eight amino acids in lenght and exhibits binding to RG2 glioma cells.

5. A pharmaceutical composition comprising the synthetic peptide of claim 4.

6. A synthetic peptide containing the amino acid sequence DLTK (SEQ ID NO:52), wherein said synthetic peptide is eight amino acids in lenght and exhibits preferential binding to glioma cells when compared to its binding to astrocytes.

7. A pharmaceutical composition comprising the synthetic peptide of claim 6.

8. The synthetic peptide of claim 6, consisting of the amino acid sequence DLTKSTAP (SEQ ID NO:43), wherein said synthetic peptide exhibits preferential binding to RG2 glioma cells when compared to its binding to astrocytes.

9. A synthetic peptide containing the amino acid sequence DMTK (SEQ ID NO:52), wherein said synthetic peptide is eight amino acids in lenght and exhibits preferential binding to glioma cells when compared to its binding to astrocytes.

10. A pharmaceutical composition comprising the synthetic peptide of claim 9.

11. A pharmaceutical composition comprising the synthetic peptide of claim 1.

12. A pharmaceutical composition comprising the synthetic peptide of claim 2.

13. A pharmaceutical composition comprising the synthetic peptide of claim 3.

* * * * *

UNITED STATES PATENT AND TRADEMARK OFFICE
CERTIFICATE OF CORRECTION

PATENT NO.        : 7,094,868 B2
APPLICATION NO.   : 10/357929
DATED             : August 22, 2006
INVENTOR(S)       : Samoylova et al.

It is certified that error appears in the above-identified patent and that said Letters Patent is hereby corrected as shown below:

Column 1; Line 24
"Ill" sould read --IL--

Column 11; Line 26
"to and various" should read --to various--

Column 45; Line 56
"lenght" should read --length--

Column 45; Line 62
"lenght" should read --length--

Column 46; Line 50
"lenght" should read --length--

Signed and Sealed this

Twenty-sixth Day of December, 2006

JON W. DUDAS
*Director of the United States Patent and Trademark Office*

SEQUENCE LISTING

```
<160> NUMBER OF SEQ ID NOS: 54

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide

<400> SEQUENCE: 1

Val Asp Leu Pro Glu His Gly Lys
 1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic peptide

<400> SEQUENCE: 2

Val Asp Lys Pro Gln His Gly Gln
 1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic peptide

<400> SEQUENCE: 3

Val Gly Leu Pro Glu His Ser Ala
 1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic peptide

<400> SEQUENCE: 4

Val Asp Leu Pro Thr His Ser Ser
 1               5

<210> SEQ ID NO 5
<211> LENGTH: 8
```

```
<212> TYPE: PRT
<213> ORGANISM: Artificial Sequence
<220> FEATURE:
<223> OTHER INFORMATION: Synthetic peptide

<400> SEQUENCE: 5

Val Asp Leu Pro Glu His Arg Gln
 1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic peptide

<400> SEQUENCE: 6

Val Asp Leu Pro Thr His Gln Ser
 1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic peptide

<400> SEQUENCE: 7

Val Asp Leu Pro Thr His Asn Gln
 1               5

<210> SEQ ID NO 8
<211> LENGTH: 6
<212> TYPE: PRT
<213> ORGANISM: Artificial Sequence
<220> FEATURE:
<223> OTHER INFORMATION: Binding motif
<220> FEATURE:
<221> NAME/KEY: VARIANT
<222> LOCATION: (2)...(2)
<223> OTHER INFORMATION: can be Glycine or Aspartic acid
<220> FEATURE:
<221> NAME/KEY: VARIANT
<222> LOCATION: (5)...(5)
<223> OTHER INFORMATION: can be Glutamic acid or Threonine

<400> SEQUENCE: 8

Val Xaa Leu Pro Xaa His
 1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic peptide

<400> SEQUENCE: 9

Val Gly Leu Pro Glu His Thr Gln
 1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic peptide

<400> SEQUENCE: 10
```

```
Val Asp Leu Pro Gln His Gly Gln
 1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic peptide

<400> SEQUENCE: 11

Asp Thr Thr Lys Asn Gly Ser Gly
 1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic peptide

<400> SEQUENCE: 12

Glu Leu Arg Gly Asp Ser Leu Pro
 1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic peptide

<400> SEQUENCE: 13

Glu Val Arg Gly Asp Ser Leu Pro
 1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic peptide

<400> SEQUENCE: 14

Val Asp Leu Pro Ser His Pro Glu
 1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic peptide

<400> SEQUENCE: 15

Val Asn Leu Pro Glu His Pro Glu
 1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic peptide

<400> SEQUENCE: 16
```

```
Val Asp Leu Pro Arg Ser Asp Thr
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic peptide

<400> SEQUENCE: 17

His Thr Thr Lys Glu Gln Met Ala
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic peptide

<400> SEQUENCE: 18

Val Asp Leu Pro Gln His Gly Gly
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic peptide

<400> SEQUENCE: 19

Val Asp Leu Pro Thr His Thr Ser
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic peptide

<400> SEQUENCE: 20

Val Asn Leu Pro Glu His Ala Gln
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic peptide

<400> SEQUENCE: 21

Val Gly Leu Pro Glu His Gln Pro
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic peptide

<400> SEQUENCE: 22

Asp Thr Thr Lys Thr Ser Ala Gly
```

-continued

<210> SEQ ID NO 23
<211> LENGTH: 8
<212> TYPE: PRT
<213> ORGANISM: Artificial Sequence
<220> FEATURE:
<223> OTHER INFORMATION: Synthetic peptide

<400> SEQUENCE: 23

Asp Ser Thr Lys Ile Gly Thr Ser
 1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic peptide

<400> SEQUENCE: 24

Asp Ser Thr Lys Ala Ser Asp Ala
 1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic peptide

<400> SEQUENCE: 25

Asp Thr Thr Gln Ser Met His Thr
 1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic peptide

<400> SEQUENCE: 26

Asp Ser Thr Lys Ser Thr Asn Ser
 1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic peptide

<400> SEQUENCE: 27

Asp Ser Thr Lys Ala Val Ala Leu
 1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic peptide

<400> SEQUENCE: 28

Asp Ser Thr Lys Ser Gly Asn Met
 1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic peptide

<400> SEQUENCE: 29

Asp Thr Thr Lys Gly Pro Gly Thr
 1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic peptide

<400> SEQUENCE: 30

Asp Gly Thr Lys Met Ala Gly Gly
 1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic peptide

<400> SEQUENCE: 31

Asp Thr Thr Lys Gly Gly Asn Pro
 1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic peptide

<400> SEQUENCE: 32

Asp Asp Thr Lys His Ser Leu Pro
 1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic peptide

<400> SEQUENCE: 33

Asp Thr Thr Arg Thr His Met Pro
 1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic peptide

<400> SEQUENCE: 34

Asp Ser Thr Arg Gly Ser Pro Ala
 1               5

```
<210> SEQ ID NO 35
<211> LENGTH: 8
<212> TYPE: PRT
<213> ORGANISM: Artificial Sequence
<220> FEATURE:
<223> OTHER INFORMATION: Synthetic peptide

<400> SEQUENCE: 35

Asp Thr Thr Arg Leu Ser Asp Gln
 1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic peptide

<400> SEQUENCE: 36

Asp Asn Thr Arg Val Ala Ala Pro
 1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic peptide

<400> SEQUENCE: 37

Asp Asp Thr Arg Tyr Ser Ser Ala
 1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic peptide

<400> SEQUENCE: 38

Asp Glu Thr Leu Tyr Gly Ile Ser
 1               5

<210> SEQ ID NO 39
<211> LENGTH: 8
<212> TYPE: PRT
<213> ORGANISM: Artificial Sequence
<220> FEATURE:
<223> OTHER INFORMATION: Synthetic peptide

<400> SEQUENCE: 39

Asp Tyr Asp Met Thr Lys Asn Thr
 1               5

<210> SEQ ID NO 40
<211> LENGTH: 4
<212> TYPE: PRT
<213> ORGANISM: Artificial Sequence
<220> FEATURE:
<223> OTHER INFORMATION: Binding motif
<220> FEATURE:
<221> NAME/KEY: VARIANT
<222> LOCATION: (2)...(2)
<223> OTHER INFORMATION: can be either Threonine or Serine

<400> SEQUENCE: 40
```

Asp Xaa Thr Lys
1

<210> SEQ ID NO 41
<211> LENGTH: 3
<212> TYPE: PRT
<213> ORGANISM: Artificial Sequence
<220> FEATURE:
<223> OTHER INFORMATION: Binding motif
<220> FEATURE:
<221> NAME/KEY: VARIANT
<222> LOCATION: (2)...(2)
<223> OTHER INFORMATION: can be either Threonine or Serine

<400> SEQUENCE: 41

Asp Xaa Lys
1

<210> SEQ ID NO 42
<211> LENGTH: 4
<212> TYPE: PRT
<213> ORGANISM: Artificial Sequence
<220> FEATURE:
<223> OTHER INFORMATION: Binding motif

<400> SEQUENCE: 42

Asp Met Thr Lys
1

<210> SEQ ID NO 43
<211> LENGTH: 8
<212> TYPE: PRT
<213> ORGANISM: Artificial Sequence
<220> FEATURE:
<223> OTHER INFORMATION: Synthetic peptide

<400> SEQUENCE: 43

Asp Leu Thr Lys Ser Thr Ala Pro
1               5

<210> SEQ ID NO 44
<211> LENGTH: 8
<212> TYPE: PRT
<213> ORGANISM: Artificial Sequence
<220> FEATURE:
<223> OTHER INFORMATION: Synthetic peptide

<400> SEQUENCE: 44

Asp Thr Thr Lys Ser Thr Thr Thr
1               5

<210> SEQ ID NO 45
<211> LENGTH: 8
<212> TYPE: PRT
<213> ORGANISM: Artificial Sequence
<220> FEATURE:
<223> OTHER INFORMATION: Synthetic peptide

<400> SEQUENCE: 45

Glu Pro Val Gln Pro His Ser Thr
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic peptide

```
<400> SEQUENCE: 46

Glu Ser Arg Gly Asp Ser Tyr Ala
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic peptide

<400> SEQUENCE: 47

Asp Leu Thr Lys Ser Ser Ala Pro
1               5

<210> SEQ ID NO 48
<211> LENGTH: 8
<212> TYPE: PRT
<213> ORGANISM: Artificial Sequence
<220> FEATURE:
<223> OTHER INFORMATION: Synthetic peptide

<400> SEQUENCE: 48

Asp Thr Thr Lys Leu Thr Asn Gln
1               5

<210> SEQ ID NO 49
<211> LENGTH: 8
<212> TYPE: PRT
<213> ORGANISM: Artificial Sequence
<220> FEATURE:
<223> OTHER INFORMATION: Synthetic peptide

<400> SEQUENCE: 49

Asp Asn Ala Ile Tyr Thr Tyr Gln
1               5

<210> SEQ ID NO 50
<211> LENGTH: 8
<212> TYPE: PRT
<213> ORGANISM: Artificial Sequence
<220> FEATURE:
<223> OTHER INFORMATION: Synthetic peptide

<400> SEQUENCE: 50

Ala Ser Asn His Val Met Tyr Gln
1               5

<210> SEQ ID NO 51
<211> LENGTH: 4
<212> TYPE: PRT
<213> ORGANISM: Artificial Sequence
<220> FEATURE:
<223> OTHER INFORMATION: Binding motif
<220> FEATURE:
<221> NAME/KEY: VARIANT
<222> LOCATION: (2)...(2)
<223> OTHER INFORMATION: can be either Threonine or Leucine

<400> SEQUENCE: 51

Asp Xaa Thr Lys
1

<210> SEQ ID NO 52
<211> LENGTH: 4
<212> TYPE: PRT
```

```
-continued

<213> ORGANISM: Artificial Sequence
<220> FEATURE:
<223> OTHER INFORMATION: Binding motif
<220> FEATURE:
<221> NAME/KEY: VARIANT
<222> LOCATION: (2)...(2)
<223> OTHER INFORMATION: can be Threonine, Serine, Leucine, or
      Methionine

<400> SEQUENCE: 52

Asp Xaa Thr Lys
 1

<210> SEQ ID NO 53
<211> LENGTH: 4
<212> TYPE: PRT
<213> ORGANISM: Artificial Sequence
<220> FEATURE:
<223> OTHER INFORMATION: Binding motif

<400> SEQUENCE: 53

Asp Thr Thr Lys
 1

<210> SEQ ID NO 54
<211> LENGTH: 6
<212> TYPE: PRT
<213> ORGANISM: Artificial Sequence
<220> FEATURE:
<223> OTHER INFORMATION: Binding motif
<220> FEATURE:
<221> NAME/KEY: VARIANT
<222> LOCATION: (2)...(2)
<223> OTHER INFORMATION: can be either Leucine, Serine, or Valine

<400> SEQUENCE: 54

Glu Xaa Arg Gly Asp Ser
 1               5
```